(12) United States Patent
Solem

(10) Patent No.: US 8,216,261 B2
(45) Date of Patent: Jul. 10, 2012

(54) TISSUE PENETRATION DEVICE AND METHOD

(75) Inventor: Jan Otto Solem, Bjarred (SE)

(73) Assignee: Synergio AG (CH)

( * ) Notice: Subject to any disclaimer, the term of this patent is extended or adjusted under 35 U.S.C. 154(b) by 293 days.

(21) Appl. No.: 12/595,568

(22) PCT Filed: Apr. 14, 2008

(86) PCT No.: PCT/EP2008/054516
§ 371 (c)(1),
(2), (4) Date: Mar. 18, 2010

(87) PCT Pub. No.: WO2008/125668
PCT Pub. Date: Oct. 23, 2008

(65) Prior Publication Data
US 2010/0179633 A1     Jul. 15, 2010

(30) Foreign Application Priority Data

Apr. 13, 2007 (WO) ............... PCT/EP2007/053658

(51) Int. Cl.
*A61B 17/22* (2006.01)
*A61B 17/32* (2006.01)
*A61F 2/06* (2006.01)

(52) U.S. Cl. .................. 606/159; 606/167; 623/1.23

(58) Field of Classification Search .......... 623/1.23; 606/159, 167, 198
See application file for complete search history.

(56) References Cited

U.S. PATENT DOCUMENTS

| 5,593,434 A | 1/1997 | Williams |
| 6,800,085 B2 | 10/2004 | Selmon et al. |
| 2007/0032808 A1 | 2/2007 | Anwar et al. |

FOREIGN PATENT DOCUMENTS

| WO | 94/21196 A2 | 9/1994 |
| WO | 98/22045 A1 | 5/1998 |
| WO | 01/76678 A1 | 10/2001 |
| WO | 2006/036690 A1 | 4/2006 |

*Primary Examiner* — Thomas J Sweet
*Assistant Examiner* — Jason-Dennis Stewart
(74) *Attorney, Agent, or Firm* — Akerman Senterfitt

(57) ABSTRACT

A medical device for canalization of a tissue of a body portion by penetration thereof, a kit, a manufacturing method and a method of canalization are disclosed. The device is adapted for trans-catheter delivery to the body portion, and comprises a radially expandable and crimpable or collapsible substantially tubular member that has a rear end, a front end, and a pattern of struts or a mesh of wires arranged in-between the rear end and the front end, arranged around an interior of the device. The tubular member has extensions, which are arranged towards the interior of the device in a first state of the device, and towards an exterior of the medical device in a second state of the device, wherein the second state of the medical device is the tubular member turned inside out. During storage, the device is restrained in a delivery catheter in the second state. During delivery the device turns outside in and digs into the tissue to create a channel therein, thus preventing or fixating debris or other matter to spread from the channel.

25 Claims, 17 Drawing Sheets

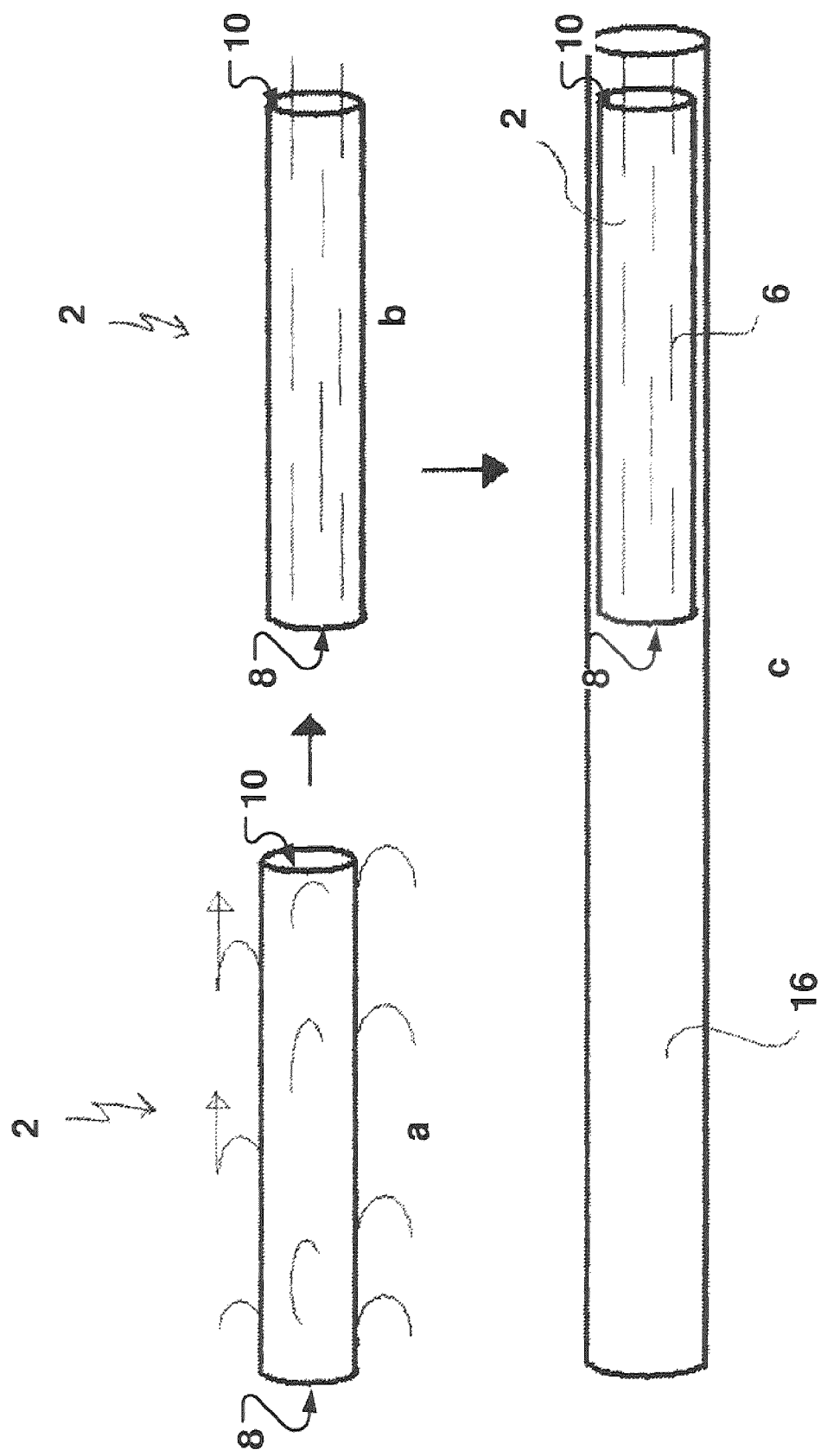

TISSUE PENETRATION DEVICE AND METHOD

FIELD OF THE INVENTION

This invention pertains in general to the field of medical devices. More particularly, the invention relates to implantable medical devices, and more particularly to implantable medical devices deliverable through the vascular system to a target site, and even more particularly to an implantable medical device for tissue penetration in order to treat a diseased human being by means of a catheter technique.

BACKGROUND OF THE INVENTION

In several conditions penetration of solid tissue is indicated in order to treat diseases or correct anomalies in a human body. Some of these conditions will be mentioned here in order to put the here presented innovation into perspective.

The simplest and most used method for penetrating tissue is by means of needles. Punching a needle through solid tissue may connect one compartment of the body with another. The needle will allow a wire or a catheter to be advanced into the next compartment through a central lumen and if necessary followed by a balloon in order to widen the created channel.

Additionally a stent, a net-like metal vessel wall support, may be inserted in order to ensure a persistent open connection. Thus, insertion of a stent is dependent upon an opening being present into which the stent may be advanced before its expansion. However, there is a need for a device and method providing penetration of solid soft tissue of a body where no channel or opening is present, or where an existing passage or channel has been blocked. The penetration is desired to e.g. provide a passage or channel in the solid soft tissue.

Medical conditions where solid tissue penetration and creation of openings or canalization thereof is needed are many and only a few can be mentioned here. Cardiac anomalies are not uncommon, in some instances connections between compartments, e.g. vessels and heart chambers, has to be created by means of surgery or catheter technique.

Ischemic heart disease caused by coronary artery narrowing's or occlusions is one of the most common heart diseases and the most common reason for death in the western world. 15 Millions diagnostic coronary artery angiograms are performed each year in the world for this reason. 12-13 Millions of these investigations reveal artery obstructions requiring an intervention to ensure good blood flow in the coronary arteries. 70-75% of the interventions today are done by catheter technique, percutaneous coronary intervention (PCI). Through the narrowing, known as stenosis, in a coronary artery a guide wire is passed, then the stenosis is dilated by means of a balloon and thereafter a mesh of metal wire formed as a metal mesh tube, known as a stent, is inserted at the treatment site in order to keep the vessel wall from collapsing at the treated site while healing occur.

30% of the coronary angiograms, however, show a chronic total occlusion (CTO) of a coronary artery where it is impossible to pass the occlusion with a needle, a guide wire or a balloon to dilate the occluded spot in the artery. Those patients have only the option of undergoing open heart surgery, being subjected to the coronary artery bypass grafting procedure (CABG).

A PCI usually implies that the patient is discharged from the hospital the same day or the day after and may return to daily activities immediately. A CABG, however means at least one week stay in a hospital and thereafter weeks or months in rehabilitation before returning to normal activities and work. With the newly introduced drug eluting stent technology, the result after PCI and CABG are comparable, however, since the PCI is by far the least invasive it would be preferable in all cases if possible. A demand for methods to pass CTO therefore is imminent, to convert cases from CABG to PCI procedures.

The extensive plaque formation of a chronic total occlusion typically has a fibrous cap surrounding softer plaque material. Such a fibrous cap may present a surface which may be difficult to penetrate with a conventional guidewire. In such instances, the typically flexible distal tip of the guidewire may be unable to cross the lesion, and in order to successfully cross and treat a chronic total occlusion, alternative devices may be required. For example, at a minimum, a stiffer guidewire may be required to traverse the stenosis. Or, an atherectomy device may be required to penetrate the occlusion. Hereinafter, applicants refer to any device intended to penetrate the occlusion, including a guidewire, as a canalizing device or a recanalizing device.

In the event that a canalizing device and/or greater force by the clinician are required in order to create a passageway through a chronic total occlusion, additional precautions must be taken to prevent injury to the vessel wall. Furthermore measures have to be taken as well to prevent debris from the CTO plug to spread with the blood stream, which otherwise might lead to undesired patient damage.

WO0176678A1 discloses an apparatus and a method for the treatment of an occluded lumen. An apparatus for centering of a device which is intended to penetrate a severe occlusion of a body lumen is disclosed. A device is disclosed that provides back support for a recanalizing device during attempts to penetrate an extensive occlusion. A catheter with a substantially central lumen for receiving a guidewire and/or other recanalizing device is provided. An embodiment disclosed also comprises a central lumen for receiving a second catheter for the purpose of conducting an angioplasty procedure and/or delivering a stent. WO0176678A1 discloses a conventional way of penetrating through an occlusion with a wire, inserting a balloon into the channel thus created, inflating the balloon for widening the channel, and inserting a stent for keeping the channel open. Debris is created when traversing the occlusion, which may harm the patient.

US20070032808A1 discloses a system and method for addressing total occlusion in a vascular environment, wherein an apparatus for addressing an occlusion in a vascular environment is provided that includes a wire and a tip coupled to the wire and operable to burrow into an occlusion in a vascular environment. The apparatus also includes a coil section disposed between the wire and the tip and operable to collect debris generated by burrowing of the tip. In US20070032808A1 conventional material removal technique comprising advancing through the hard fibrotic tissue cap is disclosed. Furthermore, debris is created when traversing the occlusion, which is handled by special measures in order to provide patient safety.

However, there is a need for an improved method, system, or device avoiding creating debris when penetrating through a CTO plug.

Since recently two products are available for clinical investigations. LuMend Inc. is offering the Frontrunner™, a catheter based device with inverted pliers at the tip. The tip is advanced after each opening of the pliers jaw. The tissue inside the CTO is forced open a little, letting the canalization device advance a step until the jaws are opened again.

U.S. Pat. No. 6,800,085 assigned to LuMend Inc. discloses this method and apparatus for treating vascular occlusions in detail. An intravascular catheter system for the treatment of occluded blood vessels that includes tissue displacement or hinged expansion members that are movable from a closed to an open position are disclosed in U.S. Pat. No. 6,800,085. The tissue expansion members can stretch apart, tear or otherwise disrupt a vascular occlusion sufficiently to create a pathway that provides a support for the passage or placement of a guidewire or an interventional vascular device across the occlusion or obstruction. However, when the system of U.S. Pat. No. 6,800,085 is used, it does, amongst others, not prevent debris from the occlusion to spread with the blood stream. This is, as mentioned above, not satisfactory with regard to patient safety.

Another system for treating vascular occlusions, the Safe-Cross offered by Translumina Inc. is also catheter based. The tip of this device is provided with a laser sensor as well as with a high frequency radio wave transmitter (RF), creating heat at the tip. The laser will by means of a computer and its software guide the tip from not penetrating the lumen of the vessel and the RF will heat the tip, burning its way through the tissue.

These prior known methods are expensive, very time consuming, risky and lead to a successful penetration of a CTO in 50% of the cases that could not be penetrated with conventional means like guide wire and balloons. Both methods and devices create debris when penetrating through a CTO plug, which is not desired.

Hence, an improved method and/or device for creating connections, openings, or canals in the body would be advantageous, and in particular such a method and/or device allowing for increased flexibility, cost-effectiveness, and/or patient safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination, by providing a device, a kit, a manufacturing method, and a canalization method, according to the appended independent patent claims.

According to aspects of the invention, a canalization medical device in form of an implant, a kit comprising such an implant, a manufacturing method for such an implant, and a method for solid biological tissue penetration and canalization thereof, e.g. for establishment of connections between compartments, are provided.

Further embodiments of the invention are defined in the dependent claims, wherein features for the second and subsequent aspects of the invention are as for the first aspect mutatis mutandis.

Some embodiments of the invention provide for an advantageous approach for creating channels in the body. Some embodiments of the invention provide an advantageous approach to treating chronic total occlusion (CTO) of a coronary artery.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 11-14: are schematic illustrations of a manufacturing method demonstrating how a an embodiment of a canalization device is manufactured and assembled into a treatment kit;

DESCRIPTION OF EMBODIMENTS

Figure 1:
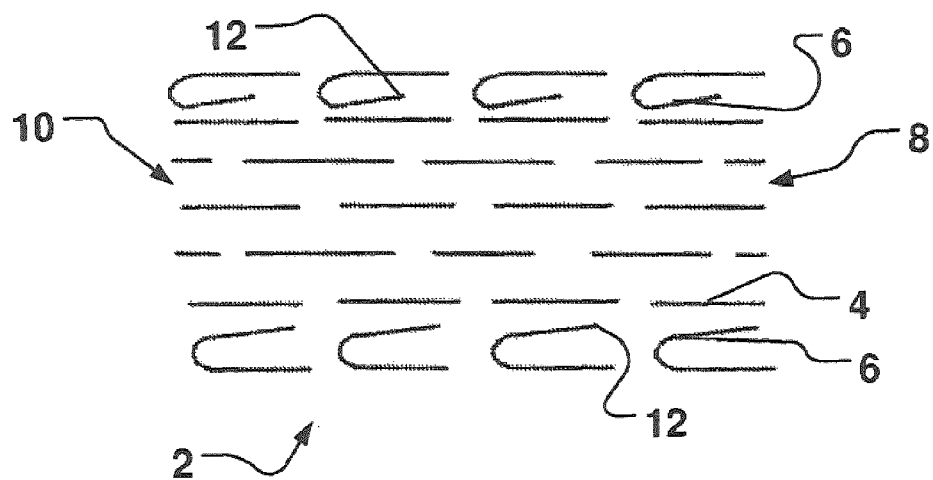
FIG. 1: is a schematic illustration of an embodiment of the canalization device 2, in the form of an implant, in the first, preferred, state.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to treatment of an occlusion of a coronary vessel, and in particular to a CTO. However, this is merely done for the sake of simplicity and it will be appreciated that the invention is not limited to this application but may be applied to many other body portions, including for example canalization of the liver. Here new connections are for instance made, by means of a canalization device, between the porta vein and the inferior vena cava in order to allow blood to flow from the porta system to the cava system in order to treat portal hypertension. In the liver also, treatment of biliary stasis due to obstructions is treated by means of tissue penetration. Incurable cancer may be penetrated, by means of a canalization device, to create connections for palliation for instance in the esophagus.

Embodiments of the here presented innovation may be used in order to provide new channels or connections of existing channels. Thus, the canalization device may be used for canalization or recanalization of body passages, i.e. in some embodiments the canalization device is a recanalization device. Both types of devices are in this specification referred to as canalization devices.

A medical device 2 is provided in embodiments for canalization of a tissue 200, 7 of a body portion by penetration thereof. The medical device 2 comprises a radially expandable and crimpable or collapsible, substantially tubular member having a front end 8, a rear end 10, and a pattern of struts 4 or a mesh of wires arranged in-between the front end 8 and the rear end 10, arranged around an interior of the medical device 2. The tubular member has a plurality of extensions 6 that are arranged towards the interior of the medical device 2 in a first state of the medical device 2.

The tubular member is in a second state of the medical device turned inside out relative the first state and the extensions 6 are arranged towards an exterior of the medical device in the second state of the medical device 2.

In an embodiment the medical device is arranged in the second state prior to or during delivery thereof to a target site in the body to be canalized by the device, inside out with the extensions arranged towards the exterior of the device, and restrained in a restraining unit. In some embodiments the medical device 2 is arranged to return to the first state from the second state by spontaneous inversion of the canalization medical device outside in, due to shape memory or resiliency of the medical device, upon removing the restraining unit at least partly.

In embodiments the medical device is arranged for attachment of at least one other device thereto, wherein the other device may comprise an expandable balloon, a guidewire, and/or a graft. The medical device has in an embodiment the expandable balloon attached at the front end of the tubular structure, wherein the front end is arranged proximally during delivery and distally after penetration into the tissue, such that the balloon is arranged to expand the substantially tubular member upon inflation. Similarly a guide wire or graft may be attached to the tubular member. The balloon and/or guide wire is in embodiments attached at the front end in such a manner that it automatically detaches from the medical device towards an end of transition from the second state to the first state.

The tubular member of the medical device has in embodiments a cover sheet arranged thereon on at least a part of its inside and/or its outside. Alternatively, or in addition, the tubular structure of the medical device has a layer of polymer arranged on a surface thereof.

The medical device is in embodiments configured to pull itself into solid tissue upon transition from the second state to the first state, e.g. out of a delivery catheter. In embodiments, the medical device is adapted for trans-catheter delivery to the body portion.

The medical device is in embodiments made of a shape memory material, such as Nitinol, and wherein the first state of the medical device is a heat set memory shape of the medical device, formed at a heat setting temperature, and the medical device in the second state has the inside out turned shape that is formed at a temperature substantially lower than the heat setting temperature, wherein a temperature where the medical device returns to its heat set memory shape is approximately body temperature of a mammal.

In some embodiments the medical device is made of a resilient material, wherein the first state of the medical device is a relaxed shape of the medical device, and wherein the medical device is resiliently restrained in the second state in the inside out turned shape, whereby the medical device is arranged to resiliently return to the relaxed shape upon at least partial release of the restraint.

The medical device may be comprised in a kit for tissue penetration and/or shaping of channels in the tissue, or connections between tissue compartments in a body, wherein the kit further comprises a delivery catheter 16 for the medical device. The medical device is in the kit arranged inside out, radially crimped and restricted in the delivery catheter 16, with a front end 8 of the medical device 2 arranged proximally in the delivery catheter 16, and a rear end 10 of the medical device arranged distally in the delivery catheter, and wherein the extensions are arranged towards an exterior of the medical device and substantially directed towards a distal end of the delivery catheter. The kit further has a pusher 26 arranged proximally of the medical device in the delivery catheter 16. In this manner the rear end 10 of the medical device is upon pushing of the pusher 26 initially pushed out of the distal end of the delivery catheter and the medical device is configured to turn around the distal end of the delivery catheter, expand, engage with the tissue, and pull itself by means of its own force out of the delivery catheter, dig and/or cut into the tissue and turn itself outside in.

Some embodiments of the canalization device are in form of an implant having a stent design, i.e. it comprises a mesh of metal wires or struts. The majority of stent designs are made of stainless steel or another metal that has to be dilated by means of a balloon to its desired size. Some stents are self expanding, made of metals with spring effect or metals with shape memory function.

The canalization device of embodiments may be an implant that is made of a shape memory metal, such as copper-zinc-aluminum, copper-aluminum-nickel, or Nitinol, an alloy of Nickel and Titanium with shape memory. Nitinol comprises a material having superelasticity properties. Superelasticity properties means that the material may be deformed substantially without loosing its resiliency. In the deformed state the material will use its resilient forces to return to its first, preferred, state. Embodiments made of materials that have normal elasticity may loose their resiliency earlier than those of superelastic materials, when stretched or compressed. However, embodiments made of materials of normal elasticity are suitable for a variety of applications, e.g. not needing an extreme expansion rate (ratio of compressed to uncompressed dimension) of the device.

A shape memory material, such as the shape memory metals disclosed above or shape memory polymers, is a material that has two different forms, one at lower temperatures and another at higher temperatures. At the lower temperatures, e.g. below 30° C., the material is elastic and may be introduced into the body. At the higher temperatures, the material is still elastic but becomes also superelastic and assumes its preferred original shape unless the transformation to this original shape is obstructed by external stress to the material. Such external stress may for instance be a restraining catheter in which the canalization device is stored before use and from which the implant is released.

The canalization device having a stent structure may be made up of rows of struts, wherein the canalization device according to embodiments may have from one row of struts to multiple rows extending to any desired length.

A feature of certain embodiments of the canalization device having a design on basis of a stent, is the presence of forceful and sharp extensions from the ordinary stent struts that protrude away from the level of the stent struts perpendicularly. These extensions are loop-shaped in the axial direction, preferably is the curvature thereof substantially circular, in order to facilitate turning around thereof in tissue.

The extensions are in embodiments arranged for substantial radial movement in a longitudinal direction of the tubular member. The extensions have in embodiments sharp edges in a front region thereof, devised for a cutting action in the tissue, and may have a shape of spikes, loops, triangles, and/or blades.

In the first shape the extensions are extruding inwards towards the stent lumen with the tips of the extensions pointing towards the front end of the implant. From this preferred state the canalization device is transferred, when using shape memory characteristics of the device at a very low temperature, preferably close to or in the range of minus degrees Centigrade where the canalization device inherent force is low, to the second, inside out state or shape by means of turning the stent inside out.

In this second, inside out state, the extensions now protrude outwards from the stent surface and are located completely outside of the stent lumen and the extensions tips are pointed to the rear end of the canalization device. By means of crimping the implant radially and straightening the extensions by bending the extension tips forwards, towards the front end of the canalization device, when using shape memory characteristics of the device under equally cold condition, the canalization device is transferred into the definite second, inside out state or shape, and placed inside a restraining delivery device, such as a delivery catheter, ready for release therefrom into tissue. The extensions are arranged for substantial radial movement in a longitudinal direction of a substantially tubular member of the canalization device.

The delivery catheter may have a curve or a knee close to the end, whereby the deployment may be steered in a desired direction in the tissue by rotating the catheter. Alternatively, the delivery catheter may have a steerable tip in order to control delivery orientation of the canalization device, e.g. for creating curved channels in tissue. Curved channels may also be created if pre-shaped bent canalization devices are used.

When using shape memory characteristics of the canalization device and when exposed to the body temperature of approximately 37° C., the canalization device transfers into the superelastic state and its built in forces are directed towards resuming its first, preferred, state or shape. While returning to the first, preferred state or shape, the canalization device will spontaneously turn itself outside in, expand in radius and the extensions will dig into the tissue to be penetrated. In addition, the extensions will resume their curved shape.

While changing the shape from pointing straight forward in a straight line, this bending back will take place inside the surrounding tissue, facilitated by a forward edge of some embodiments of the extensions that are sharp elements, such as blades or edges, adapted to cut through tissue.

While expanding radially and bending backwards to their first, preferred, state or shape, the extensions and the struts of the canalization device are turning around the end of the delivery catheter and thereby are achieving a force vector directed forward, pulling the canalization device out of the tube and exposing the next row of extensions and struts to the tissue and the edge of the catheter.

Thus, in one continuous movement, the canalization device may engage with tissue, pull itself by means of its own force out of the delivery catheter, dig into the tissue and turn itself outside in, and furthermore increase in diameter.

The system includes a pushing rod or catheter to initially release the implant from the delivery catheter, as soon as the first extensions have engaged with tissue no more pushing is necessary and the pushing means may be extracted from the delivery catheter.

In a first embodiment of the canalization device, the extensions are made in the shape of triangular blades. In a second embodiment, the extensions may have the shape of a spike. In another embodiment the extensions may have the shape of pointed loops. Embodiments of the extensions have a front tip and forward facing edges that are very sharp and devised to provide cutting action in surrounding tissue. One embodiment may contain one single row of extensions but preferably more than one or a plurality of rows of extensions is provided, wherein one row may contain from two up to multiple extensions per row. On the other hand it is not necessary that the extensions are positioned in rows, thus other embodiments may have the extensions located diagonally or at random along the substantially tubular member of the canalization device.

In an embodiment the implant may have a balloon catheter attached to the rear end. The attachment may be made to the rear end of a strut, wherein the attachment is made in such a way that when this last strut is turning outside in, the balloon is released. Other attachments may also be made, for instance by means of a thin thread that easily will break by a very low pulling force or one that break when the balloon is inflated. The balloon catheter tip is attached to the rear end of the canalization device, while the implant is making the outside in turning, the balloon follows the rear end of the canalization device and when the deployment is finished, the balloon's position is now at the front, since the rear end has replaced the front end while the canalization device is turning over itself. Inflating the balloon will now force remaining tissue in the created channel radially outwards, e.g. towards the vessel walls, and also support the radial expansion of the canalization device in the tissue.

In another embodiment, a guide wire is attached to the rear end of the implant. Similarly to the balloon, the tip of the guide wire will be located at the front of the propagation when the outside in movement is finished, for instance allowing a unit, such as a balloon or a catheter to be passed over the wire through the interior of the tubular member of the canalization device, e.g. into an adjacent compartment in communication via another compartment via a channel created by means of the interior of the canalization device.

In yet another embodiment a flexible tube may be attached to the rear end (in the second state) of the canalization device allowing directly a tubular connection between compartments that are to be connected.

In some embodiments, combinations of a guide wire, balloons and/or tubes may be attached to the rear end of the canalization device, accordingly.

In yet another embodiment a vascular graft material may be connected in addition or alternatively to the rear end of the canalization device, making it possible to connect a vascular graft to a compartment without any suturing. Such vascular grafts may be made of PTFE (poly-tetra-fluoro-ethylen), polymers like Polyurethane, Dacron, Silicon or human or animal tissue or vessels, but not restricted to these materials.

In a further embodiment of the canalization device, the outer surface except for the extensions, is in addition or alternatively covered with a sheath or a tube made of the materials mentioned in the previous embodiment.

In yet another embodiment, the canalization device is covered on the inside with a sheath of the materials mentioned. Independent of positioning the sheath inside or outside on the canalization device, the end product will be of the type of a covered stent or a stented vascular graft when in the implanted position in the first state of the canalization device.

In a further embodiment, the canalization device is positioned in a delivery tube not longer than the canalization device itself as an alternative to the normally used delivery catheter extending outside of the patients skin surface. One or more threads or tapes connected to the front and rear end of the canalization device are running outside along the tube surface, when the outside in turning of the canalization device is completed, the threads or tapes will be inside the tube. Once activated, that means the first row of extensions have engaged contact with the tissue to be penetrated, the canalization device will pull itself, including the tube inside the tissue to be penetrated. With the proper designing of the struts and an over sizing, a radial expansion of the canalization device may foreshorten the canalization device considerably, thus the penetrated tissue may be foreshortened by embodiments of the canalization device, if necessary.

A method for penetrating biological tissue is presented below. A tissue penetrating canalization device that is of stent design is provided in embodiments.

A feature of some embodiments of the canalization device having the presented stent design is the presence of forceful and sharp extensions from the ordinary stent struts that protrude away from the level of the stent struts perpendicular. These extensions are loop-shaped in the axial direction, preferably is the curvature thereof substantially or absolute circular to facilitate turning around in tissue. In the first, preferred, state or shape, the extensions are protruding inwards towards the stent lumen with the tips of the extensions pointing towards the front end of the implant. From this first, preferred, state the canalization device is transferred at a very low temperature, preferably close to or in the range of minus degrees Centigrade when the canalization device inherent force is low to the first, non-preferred, inside-out state or shape by means of turning the stent inside out.

In this second, non preferred, inside out state the extensions now protrude outwards from the stent surface and are located completely outside of the stent lumen and the extensions tips are pointed to the rear end of the canalization device. By means of crimping the implant radially and straightening the extensions by bending the extension tips forwards, towards the front end of the canalization device under equally cold condition the canalization device is transferred into the definite, non-preferred, inside out state or shape and placed inside a restraining delivery catheter ready for release into tissue. The delivery catheter may have a curve or a knee close to the end, thus the deployment may be steered in a desired direction in the tissue by rotating the catheter. When exposed to the body temperature of 37 degrees C., the canalization device transfers into the superelastic state and its built in forces are directed towards resuming its first, preferred, state.

While returning to the first, preferred, state or shape, the canalization device will spontaneously turn itself outside in, expand in radius and the extensions will dig into the tissue to be penetrated. The extensions will resume their curved shape. While changing the shape from pointing straight forward in a straight line, this bending back will take place inside the tissue since the forward edge of the extensions are sharp blades and cut easily through tissue. While expanding radially and bending backwards to their first, preferred, state or shape, the extensions and the struts are turning around the end of the delivery catheter and thereby achieve a force vector directed forward, pulling the canalization device out of the tube and exposing the next row of extensions to tissue and the edge of the catheter.

Thus, in one continuous movement the canalization device, in form of an implant, will engage with tissue, pull itself by means of its own force out of the delivery catheter, dig into the tissue, turn itself outside in and expand in diameter.

The system includes a pushing rod or catheter to initially release the implant from the delivery catheter, as soon as the first extensions have engaged with tissue no more pushing is necessary and the pushing means may be extracted from the delivery catheter. By means of engaging a first row of extensions with the tissue to be penetrated, the whole implant will pull itself into the tissue and connections may be established between compartments by means of balloons tubes and grafts using the central lumen created by means of the here presented implant.

A method for penetrating biological tissue is presented now in more general terms and with an illustrating specific, but non-limiting, example below.

The method is in embodiments a method of tissue penetration and/or shaping of channels in tissue, or connections between tissue compartments in a body portion by means of a medical device for canalization thereof by penetration thereof. The method comprises delivering the medical device in a delivery catheter to the body portion; pushing a rear end of the medical device initially out of a distal end of the delivery catheter, whereby the medical device turns around a distal end of the delivery catheter, expands, engages with the tissue, and pulls itself by means of its own force out of the delivery catheter, digging and/or cutting into the tissue and turning itself outside in, and advancing into the tissue. The method thus provides for holding debris material compressed and together by the medical device after penetration thereof through the tissue. In addition, walls of a channel created may be covered with a sheet attached inside or outside to the medical device and thereby sealing off radial leakage through the medical device and thus advantageously prohibiting creation of debris and loose parts, or fixating such debris and loose parts.

The body portion may be liver tissue and the method comprises canalization of the liver tissue. The canalization is made between the porta vein and the inferior vena cava in order to allow blood to flow from the porta system to the cava system in order to treat portal hypertension. The canalization may be made through obstructions to treat biliary stasis.

The body portion may comprise cancer tissue, and the method comprises creating connections in the tissue for palliation, e.g. in the esophagus.

Specifically a method of penetrating a CTO in a coronary artery of a human being is now described. By means of standard catheter technique, a delivery catheter is passed through the skin, through the arterial vascular tree all the way to a CTO. The catheter end is pushed against the CTO and the implant is released by means of a pushing catheter or a pushing rod inside the delivery catheter. Once the front canalization device extensions dig into the CTO, the canalization device pulls itself through the tissue making an outside in turning of the canalization device over the edge of the delivery catheter.

The propagation of the canalization device through the tissue may be directed, for instance by means of turning a bent delivery catheter in the desired direction. Thus the canalization device may be used for bent canalization and thereby connection of two compartments.

On the other hand a curve may be pre-shaped during the heat setting of the first, preferred, state to fit in a curve.

A balloon catheter attached to the rear end of the canalization device will automatically be positioned at the front of the canalization device inside the created channel when the outside in turning movement is completed and may subsequently be inflated for increasing the lumen diameter of the passage.

A guide wire may be attached to the front end of the canalization device, allowing a balloon or a catheter to be advanced over the guide wire once it is located in the newly created channel.

By means of a vascular graft connected to the canalization device or sheet covers on the canalization device itself, permanent covered fluid connections may be created by the canalization device. In this manner, walls of a channel may be created with a sheet attached inside or outside to the medical device and thereby sealing off leakage through the medical device, and further prohibiting creation of debris and loose parts, or fixating such debris and loose parts. Additionally a bypass of a CTO may be created parallel to the native course of the vessel in this way.

Finally, a method for producing a canalization device is presented. The first, preferred, state or shape of the implant is fixed and set by means of heating the latter to a predetermined setting temperature according to the principles of making memory shape Nitinol devices. Then an intermediate, non preferred, inside out state or shape is created by means of turning the canalization device outside in under cool conditions and finally the canalization device is crimped, the extensions are straightened forward and configured for insertion into a delivery catheter.

Alternatively, the canalization device may first be produced as a sheath and then folded to a tube by means of welding, such as laser welding or plasma welding, or crimping, or hooking, or otherwise attaching the edges to each other. Thus, the extensions may either be folded towards the outside directly or folded towards the inside, temperature fixed and then turned inside out.

Alternatively, the first state of the tubular member may be provided as a relaxed state thereof, and shaping the tubular member to the second state may be made by turning the tubular member outside in against a resiliency thereof.

The method of producing may comprise providing a layer of polymer on a surface thereof by spraying or milling the polymer onto the surface.

Providing the tubular member may comprise providing a sheath and folding it into the tubular member and attaching the longitudinal edges of the tubular member and the sheath to each other.

The method of producing a medical device may further comprise attaching an expandable balloon, a guide wire, and/ or a graft at the front end 8 of the medical device.

The method of producing a medical device may further comprise arranging a cover sheet on an inside or outside of the medical device.

Referring now to FIGS. 1-23 embodiments of the canalization device will be described in detail.

In FIG. 1 a side projection of an embodiment of a canalization device is shown schematically in form of an implant. The implant has a design similar to a traditional stent built up from a multiple number of interconnected struts 4. Extensions 6 are provided attached to the strut structure. Alternatively, at least some of the extensions 6 may also be an integral part of the strut structure, protruding from the struts 4.

In FIG. 1 the canalization device 2 is shown in its first, preferred, state. This may be the shape that is set by means of high temperature while setting the memory of the Nitinol alloy. Alternatively, this may be the relaxed state of an elastic, resilient canalization device 2. This is the shape the canalization device will return to when released in tissue of mammal body, normally at a body temperature of approximately 37° C.

The diameter of the canalization device 2 may be chosen corresponding to the desired size of the channel to be created by means of the canalization device 2. The inner curvatures of the curved extensions 6 are open to the front end 8 and the tips 12 of the extensions are also pointed towards the front end 8 of the implant 2. The extensions 6 and their tips 12 are clearly located inside the canalization device 2.

Figure 2:
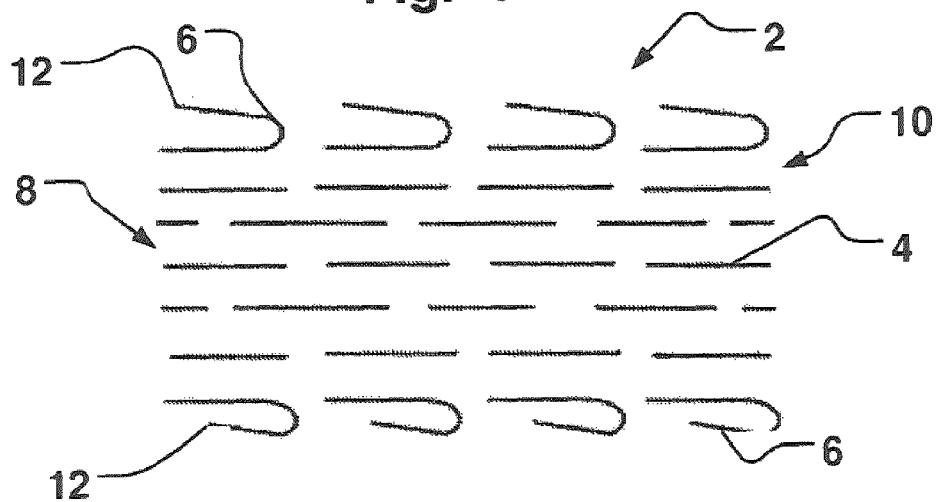
FIG. 2: is a schematic illustration of an embodiment of the canalization device 2, in the form of an implant, in the first, non-preferred, inside out state.

In FIG. 2 we see the canalization device 2 in its second, non-preferred, inside out state. In relation to the first state, the implant is turned inside out. This may be made manually or machine assisted. For instance, while cooling a Nitinol structure to low temperatures, such as at or below 0° C., it is possible to turn the whole implant inside out, e.g. manually. FIG. 2 shows the implant in the inside out shape. The extensions 6 are now on the outside of the struts 4. The inner curvatures of the curved extensions 6 are open to the front end 8 (which is now oriented backwardly) and the tips of the extensions are also pointed towards the front end 8 of the canalization device 2. The extensions 6 and their tips 12 are clearly located outside on the canalization device 2.

The terms "front end 8" and "rear end 10" of embodiments of canalization devices described herein are not intended to limit the orientation of these first and second ends which are arranged at opposed ends of the canalization device 2, due to the inside out wrapping or folding of the device. As is clear, e.g. from the drawings, the front end 8 may be oriented backwardly in some circumstances, e.g. during insertion thereof.

Referring now to the FIGS. 3 to 5, the transformation of the canalization device into the second, non preferred, inside out state of the canalization device will be described, wherein this shape change may also be made under freezing temperature.

Figure 3:
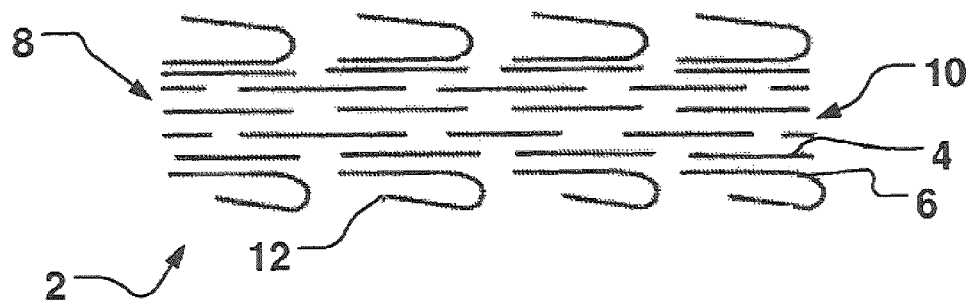
FIGS. 3-5: are schematic illustrations of an embodiment of the canalization device 2 in transfer to a second, non-preferred, inside out state.

First, as depicted in FIG. 3, the implant is crimped to a smaller diameter compared to the one in FIG. 2, in order to fit into a restraining catheter 16, which is to be used during implanting the canalization device in tissue. The implant may be crimped close to a compact rod in order to facilitate penetration of tissue in this state or when expanding from this state. In a non-limiting example, a crimped implant may have a diameter of approximately 1.5 mm and an expanded implant approximately 4 mm with a channel therein.

Figure 4:
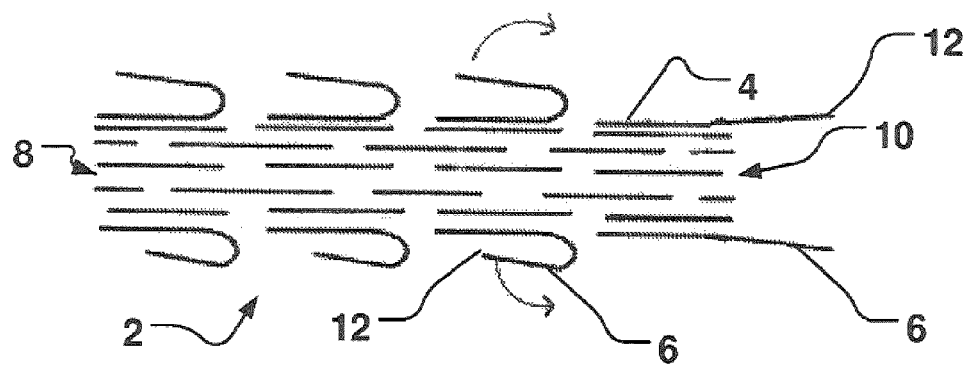

In FIG. 4 the next step of shape transformation is depicted. The extensions are bent forward so that the curvature is straightened out and the tips 12 of the extensions 6 are pointing straight forward, towards the rear end 10 (now oriented forwardly) of the canalization device 2. The extensions 6 will now be under tension in this straight shape due to the inherent resiliency of the Nitinol material.

Figure 5:
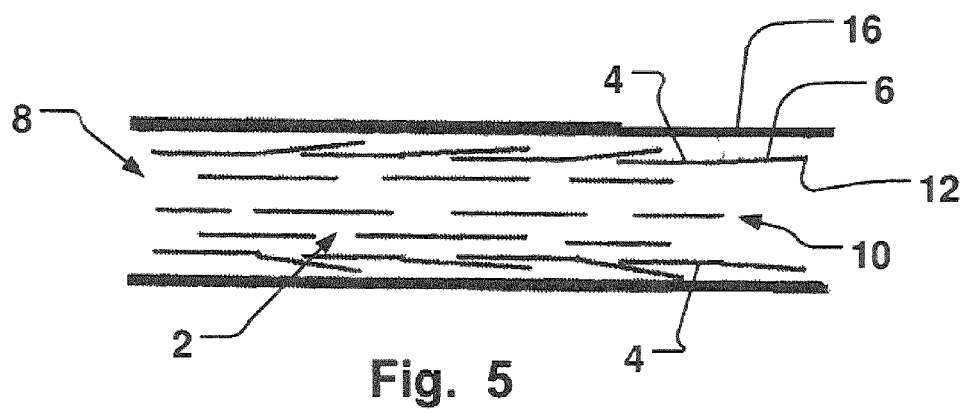

FIG. 5 shows the implant 2 positioned inside a restraining tube 16, crimped to the above-mentioned small diameter, and with all the extensions 6 straightened substantially forward, until they are substantially straight and the tips 12 are pointing in a direction extending from the front end 8 towards the rear end 10 of the canalization device. Some of the extensions 6 may protrude in this direction from the front end 8 of the implant 2. The restraining catheter 16 depicted here is shown short, in practice however, it extends outside of the skin of the human body, the implant is inserted into the front end of it and the whole catheter 16 is advanced along the interior of a vessel or inside another, larger, delivery catheter (not shown) to the area in the body where it is desired to achieve a canalization or recanalization by means of the canalization device 2.

The front part of the catheter 16 may be made of a specially hard material prohibiting that the extensions 6 dig into the wall of the catheter 16 and get stuck. Alternatively a restraining member attachable to the front end of catheter 16 may serve for storage before use. A channel providing space for a guide wire might be provided for temporary guidance to the treatment site (not shown). The restraining catheter 16 may additionally comprise an inflatable balloon on its outside over which the canalization device turns upon delivery. Inflation of this balloon may support radial expansion of the canalization device in its first state in tissue, and contribute to the avoidance of loosening of debris or other particles during canalization.

The FIGS. 6 to 13 illustrate the spontaneous transformation of the implant from the second, not preferred, inside out and crimped or collapsed state or shape of the implant 2 back to the first, preferred, and expanded state or shape thereof, when the latter is released from the restraining catheter 16 and allowed to engage with tissue 200 in the body, under approximately 37° C. body temperature.

Figure 6:
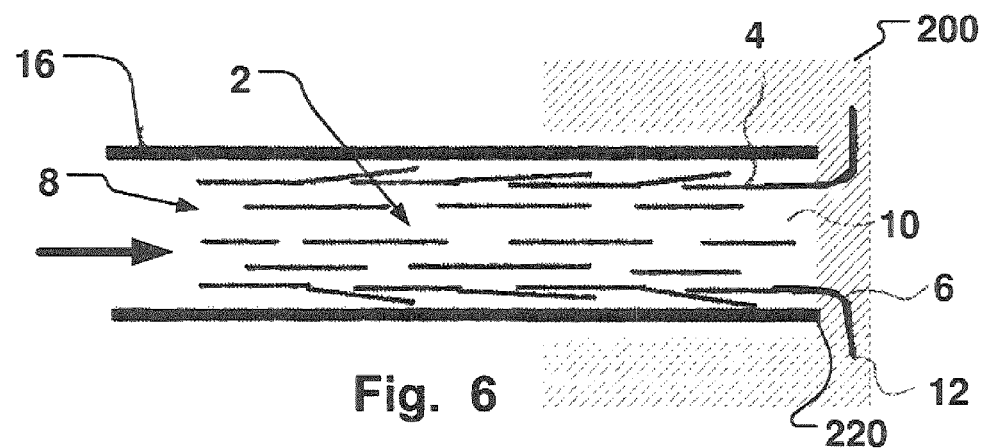
FIGS. 6 and 7a-g: are schematic illustrations of the embodiment of the canalization device 2 in spontaneous transfer from its second, non-preferred, inside out state back to the first, preferred, state.

FIG. 6 shows the very first moment of deployment and engagement with solid tissue 200 when the tips 12 of the extension 6 engage with tissue, respectively. This first movement may be initiated by means of a pusher 26, e.g. shown in FIG. 13, as indicated by the arrow on the left in FIG. 6. As soon as the first initial movement of the canalization device 2 out of the front end of the catheter 16 has taken place, the implant will pull itself out of the restraining tube and dig and/or cut into the tissue by its own force. The extensions 6 are under tension in this state, and they strive to regain their curved shape, that initially was heat set, or which is the relaxed shape thereof to which the extensions resiliently return upon release of a restriction. While doing this, they are abutting the restraining tube's front end 220, and a force vector will continue to push the implant forward out of the restraining tube's front end 220.

The FIGS. 7a to 7g describe the continuous movement that follows when the implant is freeing itself from the restraining means by its own force and returning to its first, preferred, and expanded state. FIGS. 7a to 7g are cross sectional views, wherein illustration of some struts 4 is omitted in order to simplify the drawings.

Figure 7A:
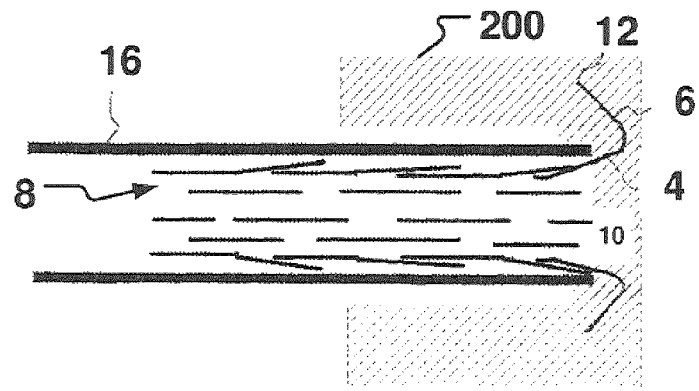

In FIG. 7a, a first extension 6 is complete inside the tissue 200 and the first row of stent struts 4 is following. The stent struts are under resilient tension due to the built in memory of shape that is set, in the Nitinol alloy of some embodiments. They strive to return to the first, preferred, state by curling or turning around the end of the restraining catheter 1. While doing this movement, the whole canalization device 2 is turning itself outside in, back to its first, preferred, expanded state or shape from the second, non-preferred, inside-out and crimped or collapsed state or shape.

Figure 7B:
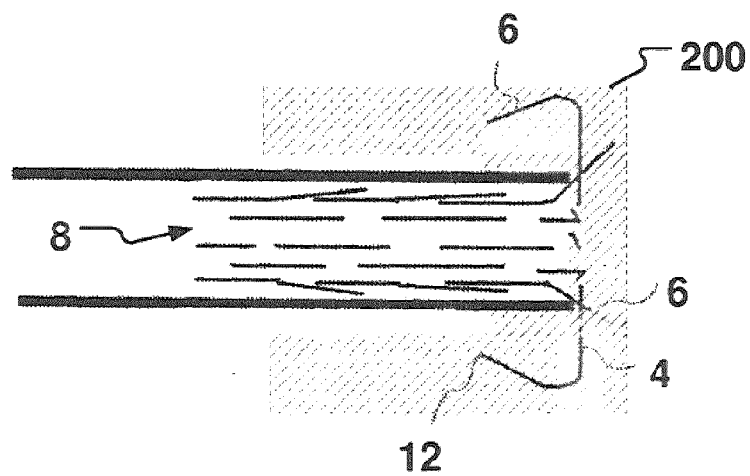

In FIG. 7b the first row of extensions 6 is dug and/or cut into the tissue and the first row of stent struts 4 are now perpendicular, half way around. The next row of extensions 6 have already engaged with tissue 200 and continue the pull, digging in and turning around movement.

Figure 7C:
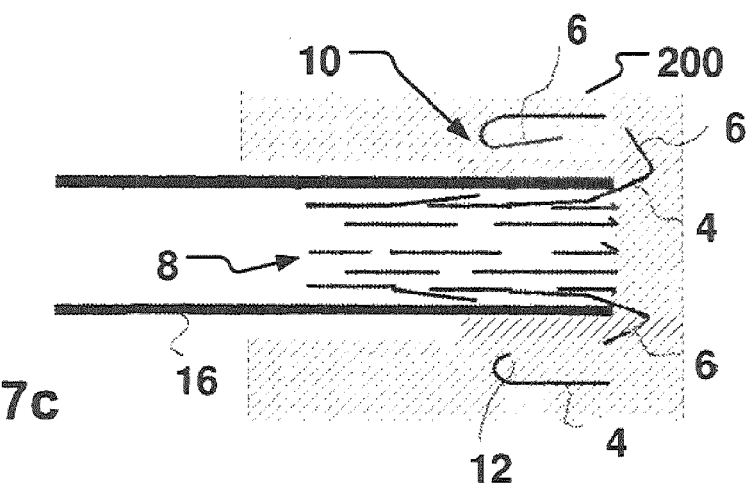

In FIG. 7c one row of extensions 6 and one row of implant struts 4 are back in the first, preferred, state. The next row of extensions 6 have already totally engaged with the tissue 200 and the second row of stent struts 4 are emerging from inside the restraining tube 16.

FIGS. 7d to 7g show the continuation of the turning over movement, back to the first, preferred, expanded state or shape.

Figure 7D:
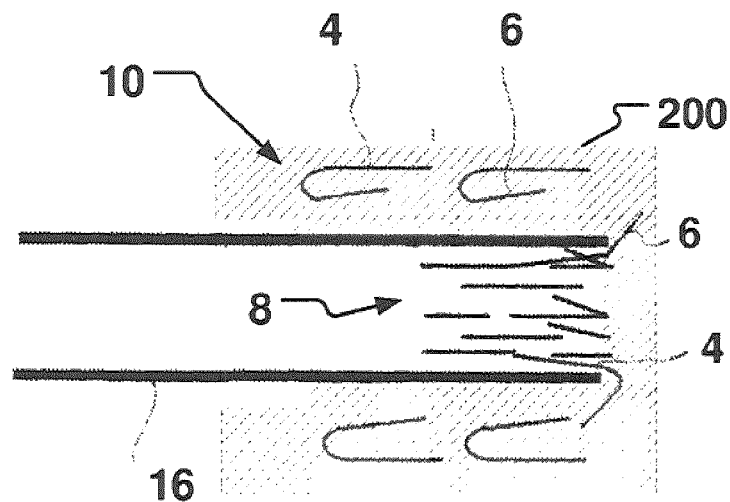
Figure 7E:
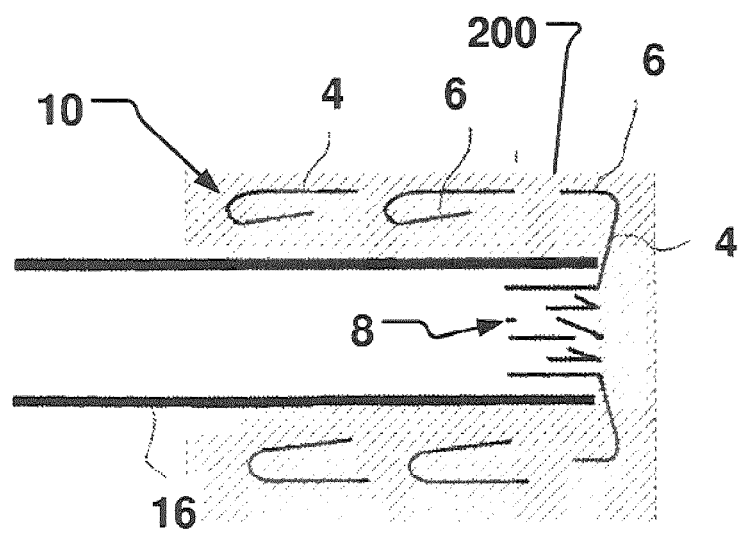
Figure 7F:
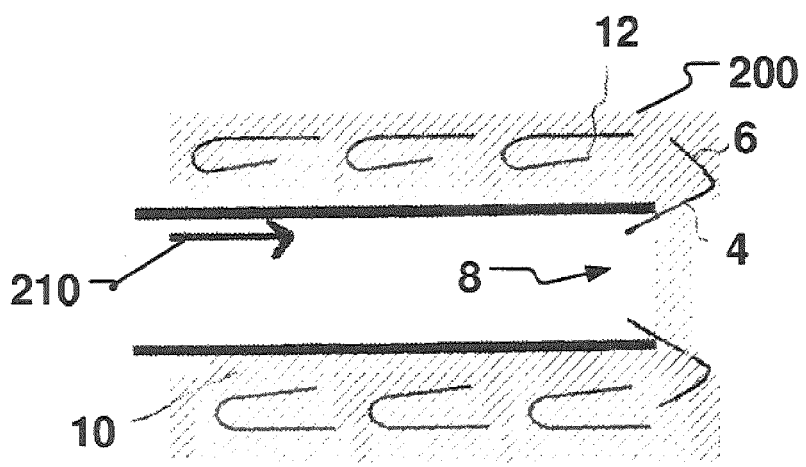
Figure 7G:
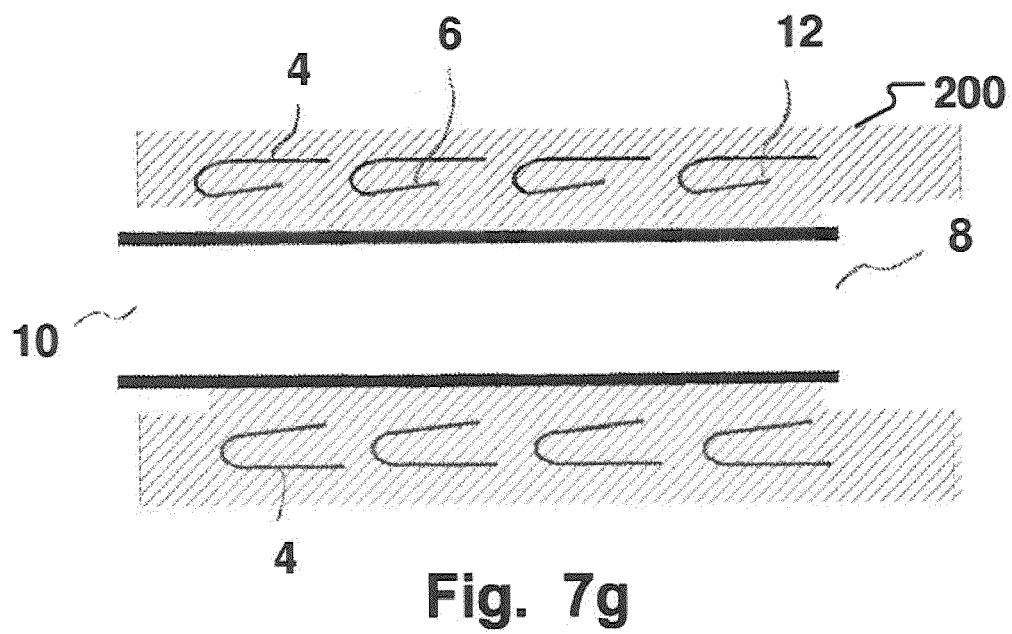

In FIG. 7d two rows of extensions 6 and two rows of stent struts 4 have turned around. In FIG. 7e almost three rows of stent struts 4 have turned around, and finally, in FIG. 7g all the four rows of extensions 6 and struts 4 have turned around. The canalization device is now back in its first, preferred, expanded state or shape, and substantially is in an identical shape to that shown in FIG. 1. The extension tips 12 are again pointing forward, wherein all the extensions 6 are inside the canalization device 2. The restraining tube 16 has been following the canalization device 2 inside the tissue, as the arrow 210 in FIG. 7f indicates. A gentle push on the outside end of the catheter may ensure that the tube follows the implant inside the tissue 200.

The struts of other embodiments of the canalization device may have other shapes, different from the ones discussed and illustrated in FIG. 1-7. In addition, the canalization device and connections 18 may have other shapes. Suitable shapes may be produced by state of the art processes in stent designs, in order to use struts that easily will turn over, ensuring the above mentioned inside out and outside in transition of the canalization device.

The canalization device may also have a predetermined bend, set as part of the first, preferred, state in order to fit tortuous occluded vessels.

Figure 8:
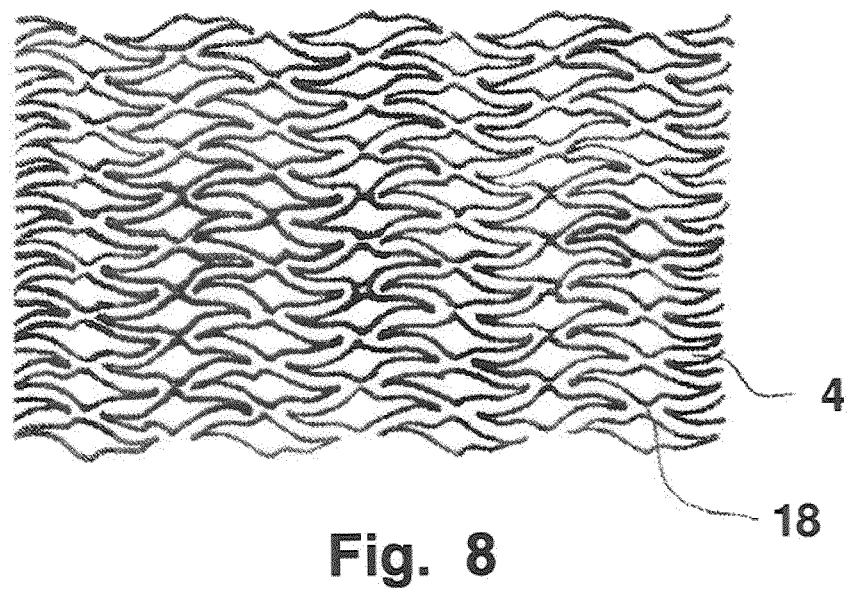
FIGS. 8-10: are schematic illustrations of other embodiments of the canalization device having a tubular stent structure that is longitudinally cut open, flattened and shown as a patterned sheet comprising various sharpened extension forms.

One example of strut patterns is shown in FIG. 8, wherein a canalization device is cut open longitudinally, flattened out and is shown as a sheet. Extensions 6 may be laser cut together with the struts out of one piece of Nitinol alloy, e.g. out of a tube, in that case the struts are integrated in the strut pattern and are in the same plane as the struts when the extensions are in a straight forward position.

Figure 9A:
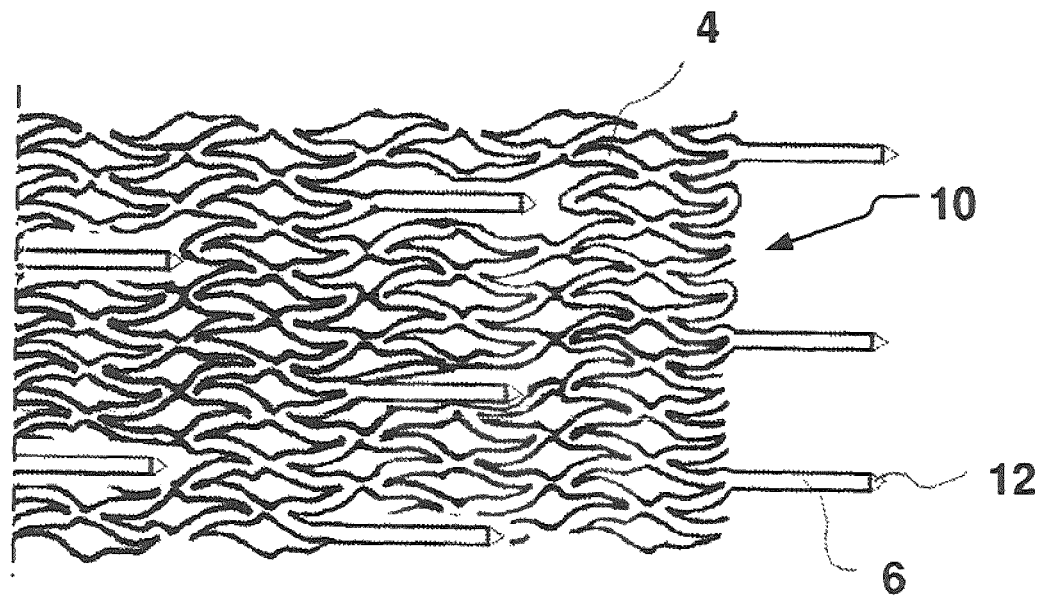
Figure 9B:
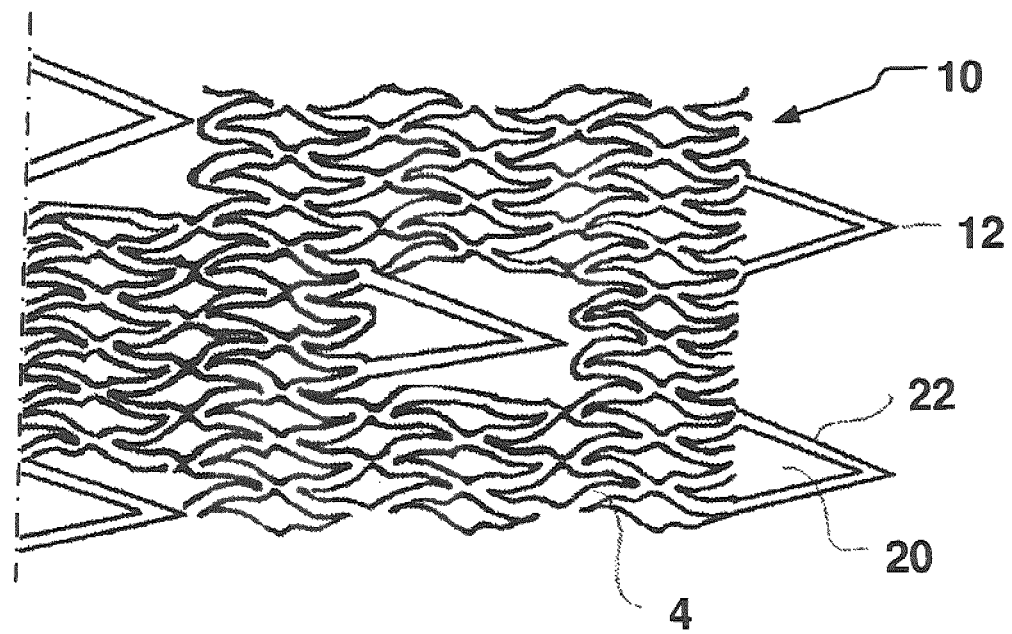
Figure 9C:
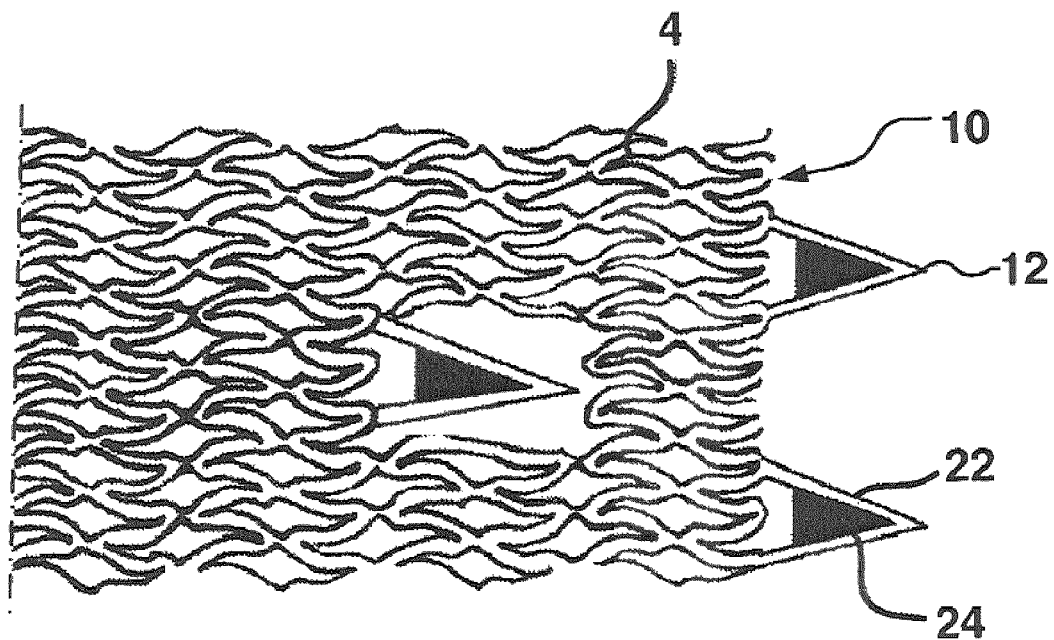

FIGS. 9a-c show implants where the extensions 6 are integrated in the strut pattern and cut in one piece. The extensions 6 may have a multiple variation of shapes, wherein three embodiments of shapes are depicted herein.

In FIG. 9a the extensions 6 have the shape of spikes with a sharp end 12. In FIG. 9b, the extensions shown have a triangular shape 20, wherein each leg has a sharpened edge 22 in the forward direction. In FIG. 9c, the shape of the extension is of a triangular blade 24, also with sharpened edges 22. In another embodiment, the extensions are not cut together with the struts in one piece and in the same level as the struts, instead they are made separately and attached to the stent surface, e.g. by soldering, welding, plasma welding, clamping, or the like attachment methods.

Figure 10:
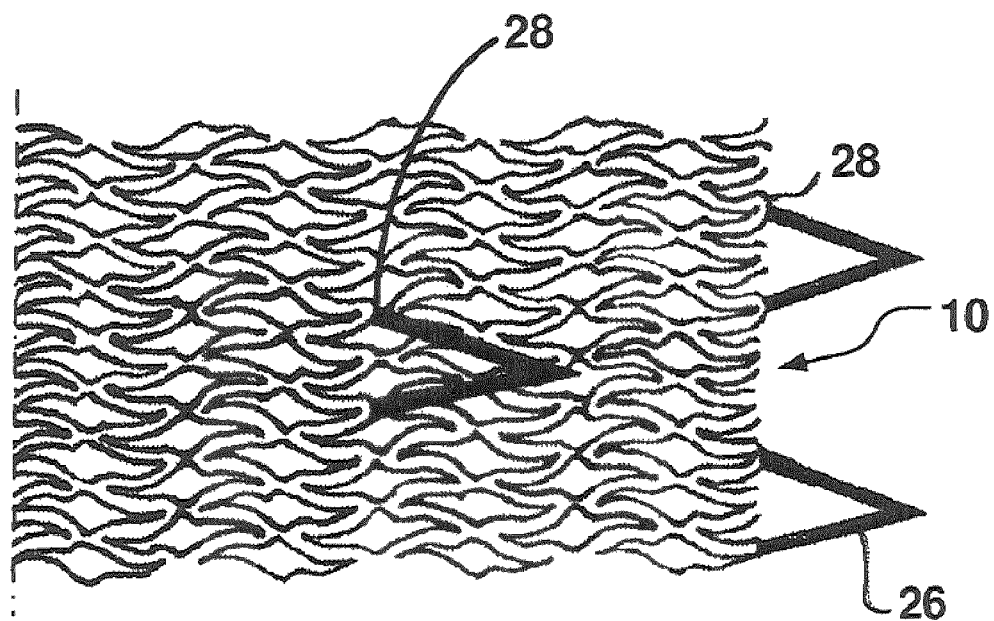

FIG. 10 shows how the pattern of the canalization device is undisturbed underneath the extensions 26, wherein the extensions are attached by welding at welding points 28. It must be noted that the here demonstrated shapes of the spikes are only examples and that an expert in the field may shape the extensions differently in a suitable manner for providing the necessary function thereof, e.g. digging and/or cutting control properties when transitioning between the two states.

The manufacturing of the canalization device is fundamental to give the canalization device the desired capabilities. The key issue here is the turning inside out of the canalization device after setting the memory of the first, preferred, shape of the canalization device. This may be done for Nitinol alloy by means of heating it to the setting temperature in an oven. While setting the shape, the canalization device is fastened in a fixture forming the extensions of the first, preferred, state as well as the canalization device. The shape is maintained by the fixture at a predetermined temperature for a predetermined period of time. After cooling the shape becomes set to the desired configuration. If this shape is disfigured, it will return to the set configuration upon heating or simply releasing the disfigured shape. The force with which a superelastic or shape memory alloy returns to a set configuration can be increased by modifying the temperature at which the configuration is set, or by modifying the period of time the alloy is maintained at the elevated setting temperature.

Figure 11:
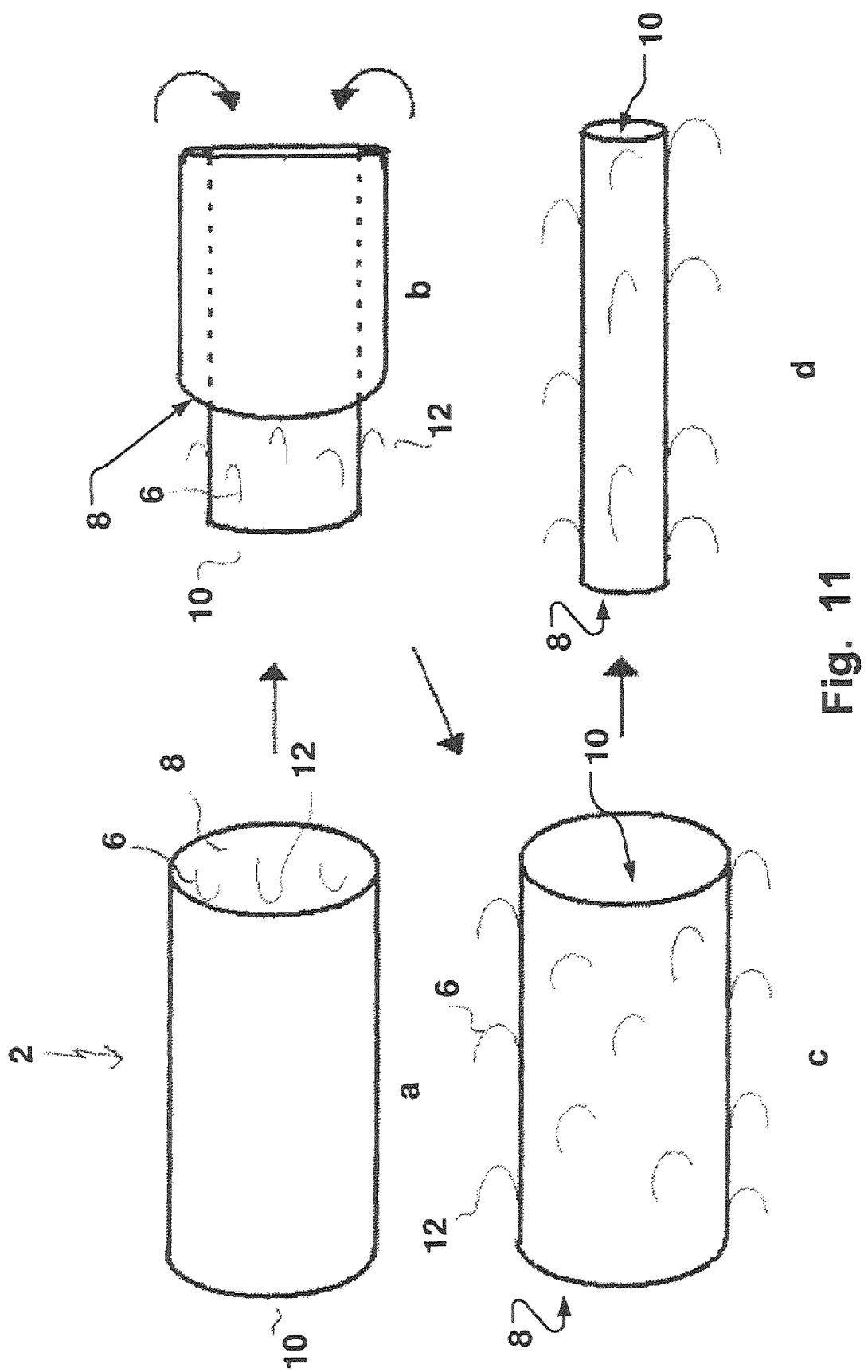

FIG. 11 demonstrates the first stage in the manufacturing procedure: FIG. 11a shows the canalization device in the first, preferred, state, wherein the extensions 6 are on the inside of the canalization device, and the tips 12 of the extensions 6 are pointing forward. In FIG. 11b, the folding over of the canalization device inside out is depicted, in part of the canalization device we may see that the extensions 6 are situated on the outside surface of the stent and pointing towards the rear end 10 of the canalization device. In FIG. 11c the turning over of the canalization device is completed, and in FIG. 11d, a manual crimping in diameter is preparing the canalization device for insertion into a restraining delivery catheter 16.

Figure 11E:
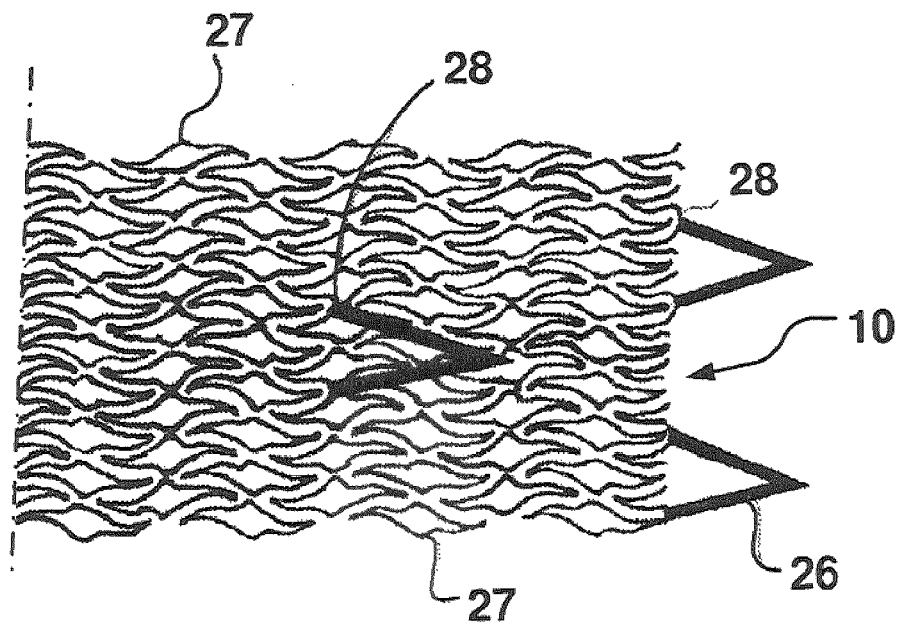

FIG. 11e depicts an alternative method for production. Now the stent is produced as a sheath with the extensions, by folding, a tube may be created either with the extensions inside or outside, finally the tube shape is secured by means of locking, attaching, or welding the edges 27 to each other.

While assembling the system by means of inserting the canalization device into the delivery catheter 16, the extensions are straightened out into a straight forward position, see FIGS. 12*a* and 12*b*, before the implant is inserted into the delivery catheter 16, FIG. 12*c*.

In FIG. 13*a* the implant 2 is illustrated as positioned in the restraining delivery catheter 16 in a position so far inside the catheter that the tips of the extensions 12 are well inside the delivery catheter, in such a manner that they may not engage with surrounding tissue that is not intended to be penetrated while being positioned by means of the delivery catheter. Since the tips 12 are inside the catheter, the canalization device 2 will have to be moved forward in the delivery catheter 16 so far that the tips 12 may engage with the tissue to be penetrated in order to activate penetration. In order to facilitate such a forward movement, a pusher rod or tube 26 may temporarily be used and then be retracted and discarded since the canalization device may after engaging the tissue pull itself further, as described above.

Figure 14:
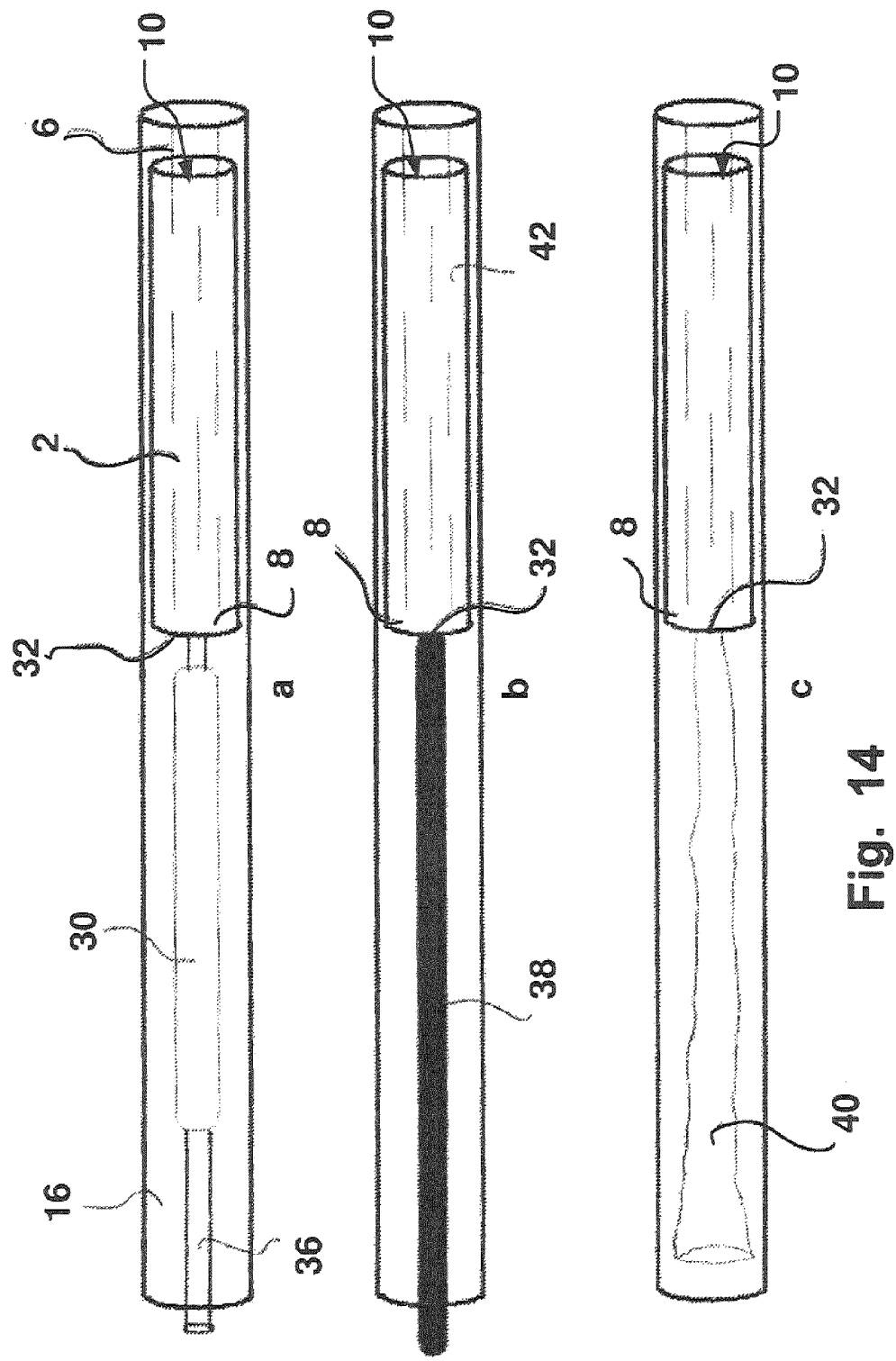

FIG. 14 is showing different kit assemblies that may be used for tissue penetration and/or shaping of channels in tissue, or connections between compartments.

FIG. 14*a* shows a balloon catheter 36 with an inflatable balloon 30 attached by means of attachment means 32 to the front end 8 of the implant 2. The attachment means may for instance be a tether line, an adhesive point, a loop etc.

FIG. 14*b* shows a guide wire attached by means of an attachment means 32 to the front end 8 of the implant 2.

FIG. 14*c* shows a vascular graft material tube 40 attached by means of an attachment means 32 to the front end 8 of the implant 2. Such vascular grafts may be made of PTFE (polytetra-fluoro-ethylen), or polymers like Polyurethane, Dacron, Silicon or human or animal tissue or vessels. In a further embodiment of the canalization device, the outer surface may, except for the extensions, be covered with a sheath or a tube 42 made of the materials mentioned in connection with FIG. 14*c*, here shown in FIG. 14*b*.

In yet another embodiment the canalization device is covered on the inside with a sheath, which may be made of the materials mentioned in the previous paragraph. Independent of positioning the sheath on the inside or outside of the canalization device, the end product will be in the form of a covered stent or a stented vascular graft when in position in the body. Alternatively, or in addition, a layer of polymer may be provided on a surface of the canalization device, for instance by spraying or milling the polymer onto the surface. In this manner a fluid tight polymer layer may be provided along the tubular member of the canalization device, without impairing the transition characteristics between the first and second state thereof.

Figure 15:
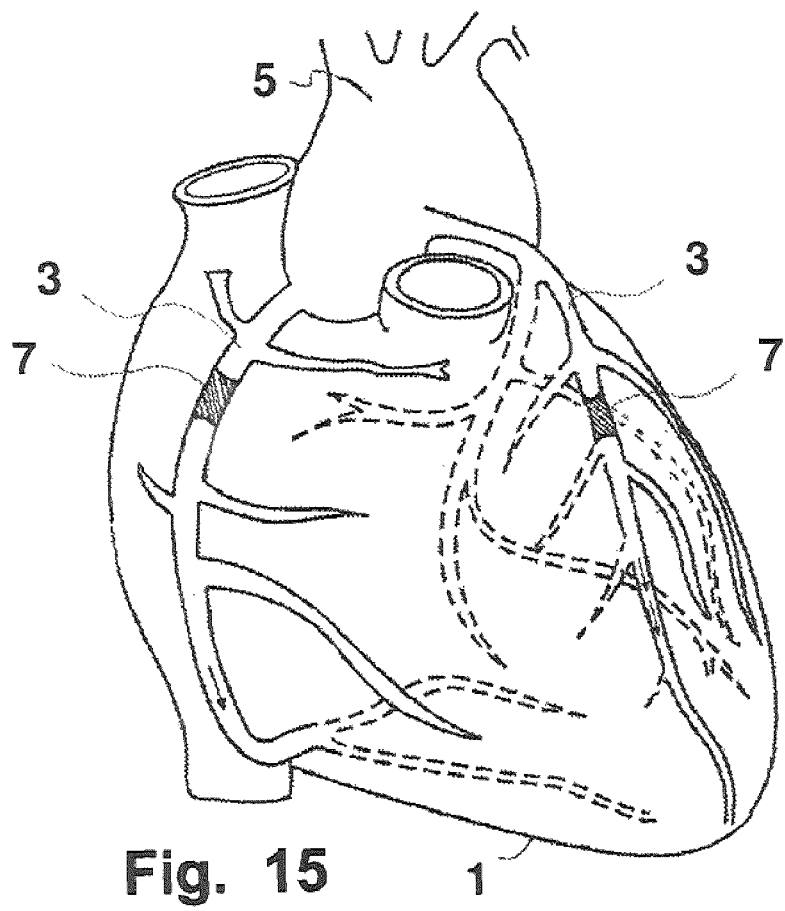
FIGS. 15-23: are schematic illustrations for demonstrating the use of an embodiment of the canalization device, in the form of an implant, which penetrates solid tissue in an example of a heart coronary artery chronic total occlusion (CTO).
Figure 13:
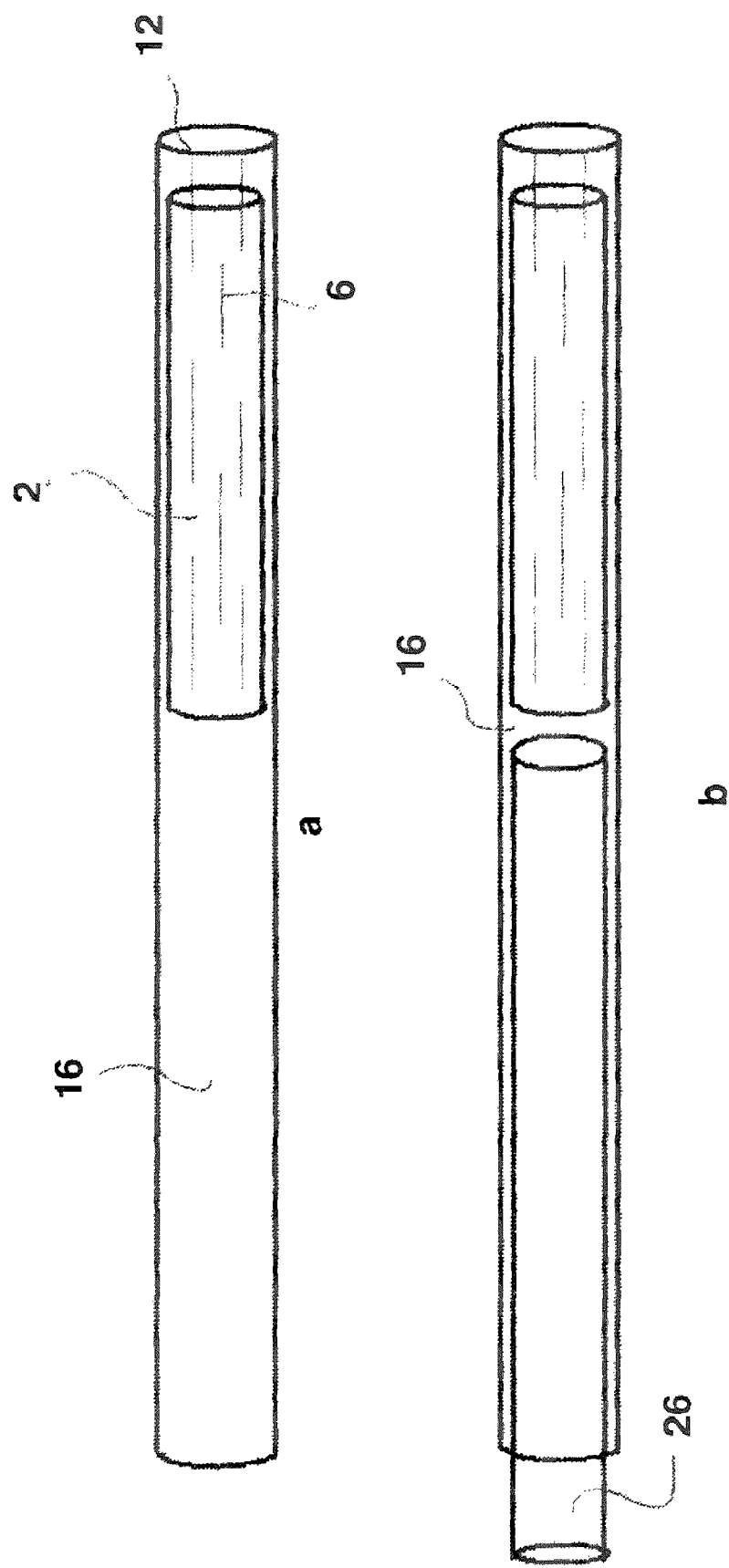

A method for penetrating solid human tissue, such as soft tissue, will now be demonstrated with reference to the following drawings. FIG. 15 shows a human heart 1, with coronary arteries 3, originating from the aorta 5. In the coronary arteries chronic total occlusions (CTO) 7 are blocking the normal blood flow indicated by arrows downstream.

Figure 16:
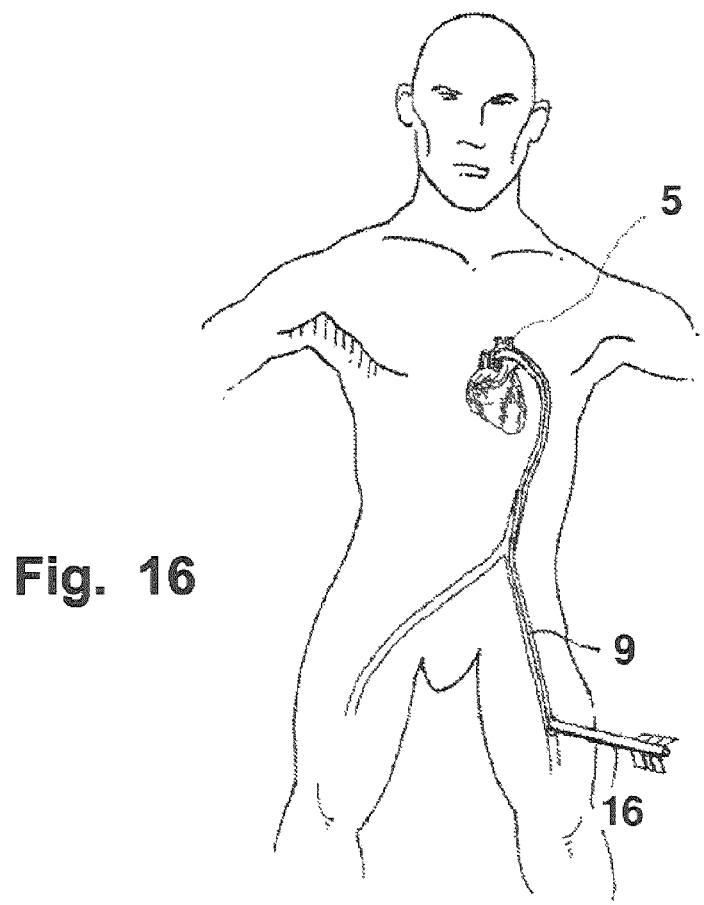

In FIG. 16 a delivery catheter 16 is put into an artery, here a femoral artery 9 as an example and follows the artery tree all the way to the ascending aorta 5 and into a coronary artery 3 until it abuts the CTO 7.

Figure 17:
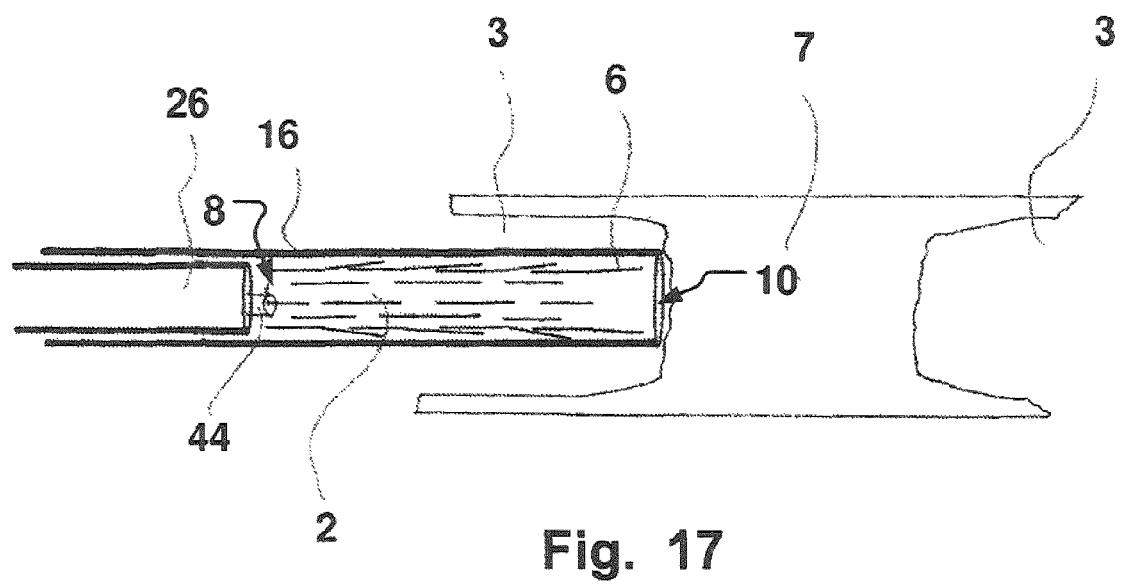

In FIG. 17 it is illustrated that the delivery catheter 16 is abutting the CTO 7, wherein the extensions 6 are still covered by the delivery catheter 16 tip. Behind the canalization device 2 inside the delivery catheter 16, a pusher 26 is available for initiating the first engagement of the extension tips with the CTO. Only the tip 44 of a balloon catheter inside the pusher tube 26 is visible.

Figure 18:
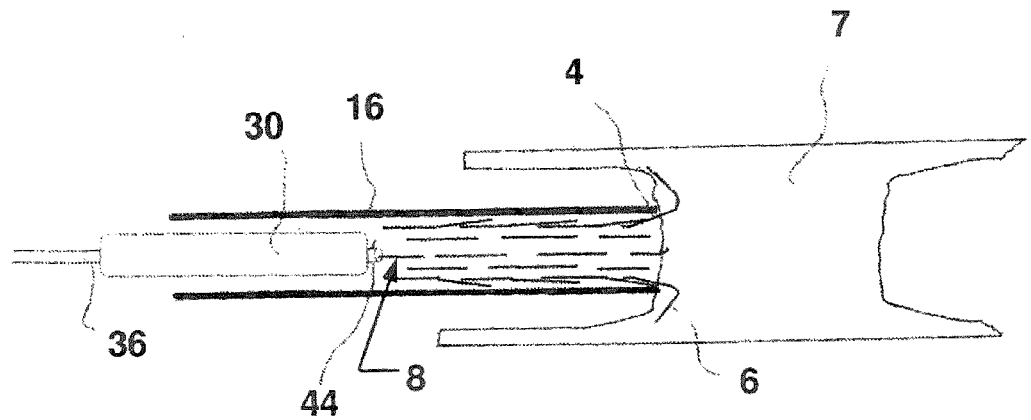

In FIG. 18 the pusher 26 has been pushed forward so much that the extension tips have engaged into contact with the CTO tissue. Often a fibrous cap surrounding is present at this outer portion of the CTO, followed by softer plaque material further inside the CTO plug. Such a fibrous cap may present a surface which has been difficult to penetrate hitherto. Thanks to the digging and/or cutting action of the shape transforming extensions, such a fibrous cap is penetrated advantageously by means of embodiments of the invention. As illustrated, the leading extensions have already engaged with the CTO tissue and have bent backwards pulling the strut 4 out, wherein the strut is already half way out in the tissue and has started turning around.

Figure 19:
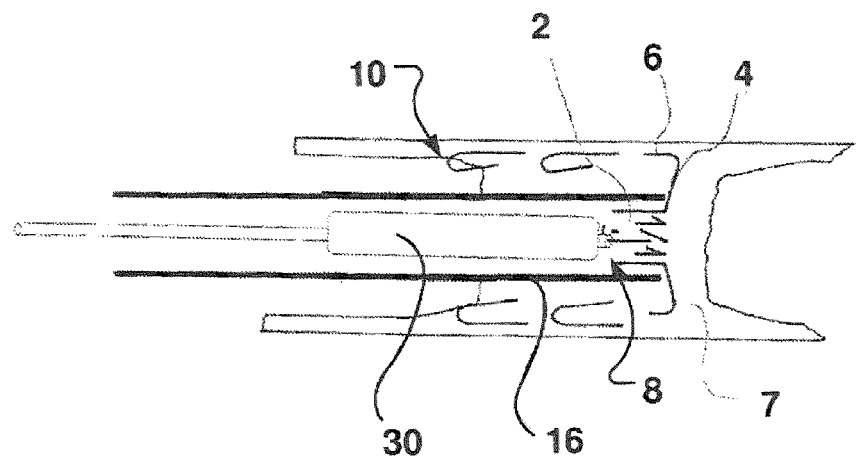

In FIG. 19 the third extension 6 is out in the tissue followed by the third strut 4 that is perpendicular to the catheter and the canalization device is close to total penetration of the CTO 7. The delivery catheter 16 and the balloon 30 are following the canalization device 2 into the CTO 7.

Figure 20:
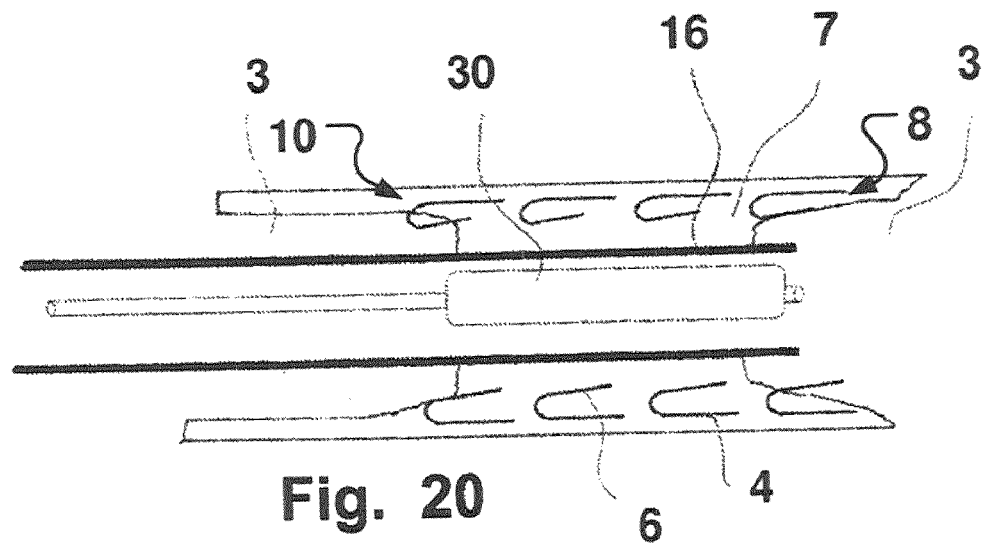
Figure 21A:
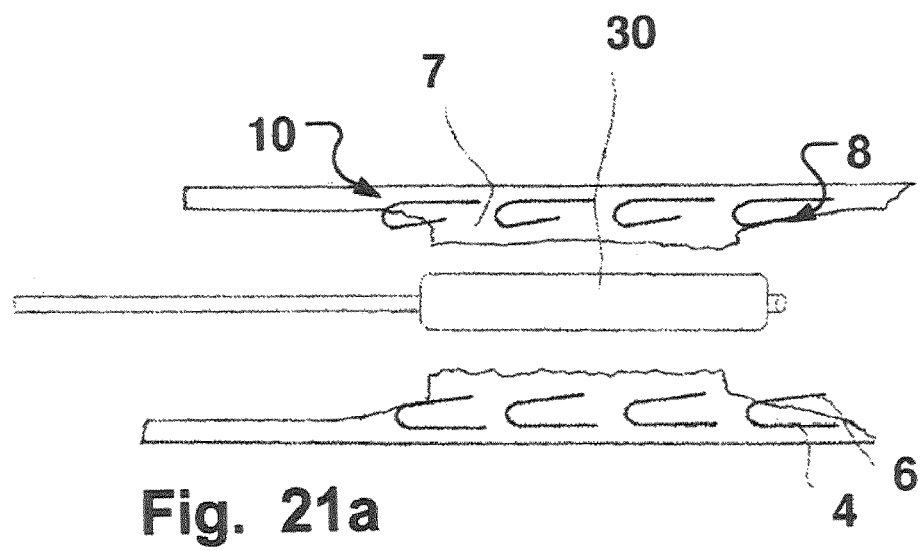
Figure 21B:
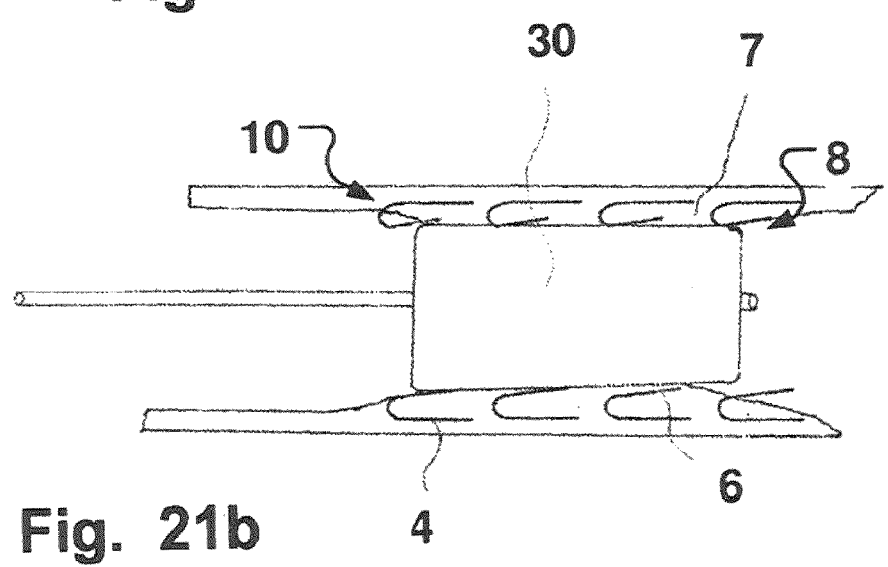
Figure 21C:
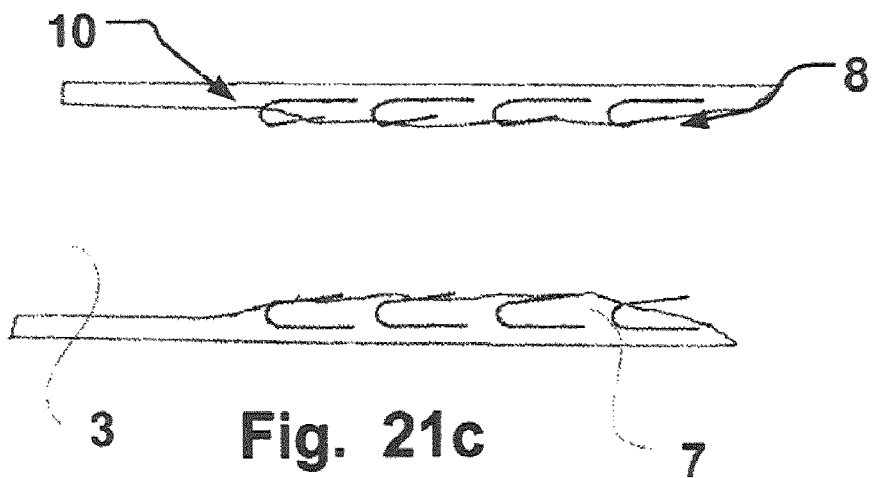

In FIG. 20 the penetration of the CTO 7 is complete and there is now a connection between the lumen of the coronary artery 3 before and after the CTO 7. The implant is returned into its first, preferred, state, as depicted in FIGS. 1 and 11*a*. In FIG. 21 the delivery catheter 16 is retracted, the balloon 30 is centered in the CTO channel and may now be inflated in order to distend the channel, which has hitherto been created by the canalization device to a larger lumen and also to distend the canalization device in order to obtain an optimal diameter where the function of the coronary vessel is restored. FIG. 21*a* illustrates the situation before and FIG. 21*b* after balloon 30 inflation. FIG. 21*c* shows a completed channel providing recanalization between the two sides of the CTO 7 in a coronary artery 3. It should be noted that no debris has been created, the CTO plaque material is compressed and hold together by the canalization device, which now is in permanent position. No measures need to be taken in order to prevent any debris from spreading with the blood flow through the vessel that is recanalized. Hence, the medical device may prohibit creation of debris and loose material or parts, or it provide additionally or alternatively fixating or trapping of such debris and loose material parts eventually dislodged from the tissue during penetration and expansion of the canalization device.

Figure 22A:
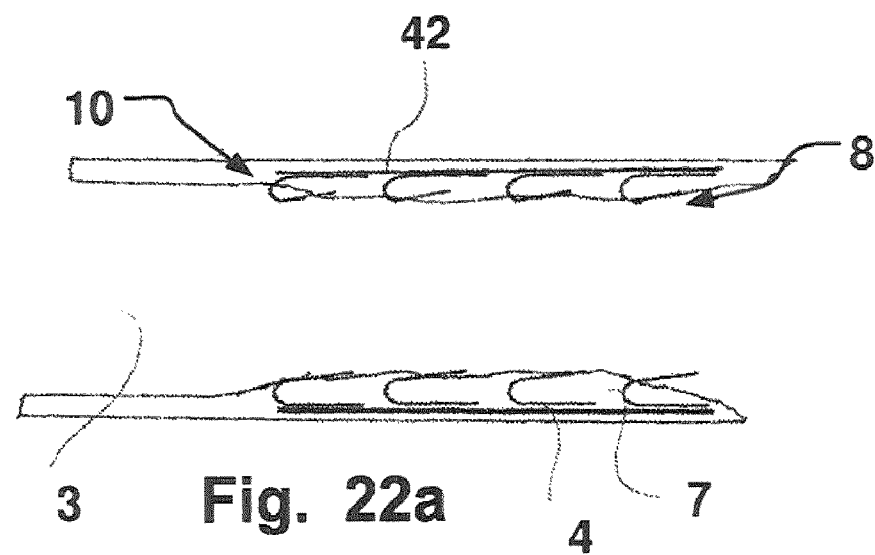
Figure 22B:
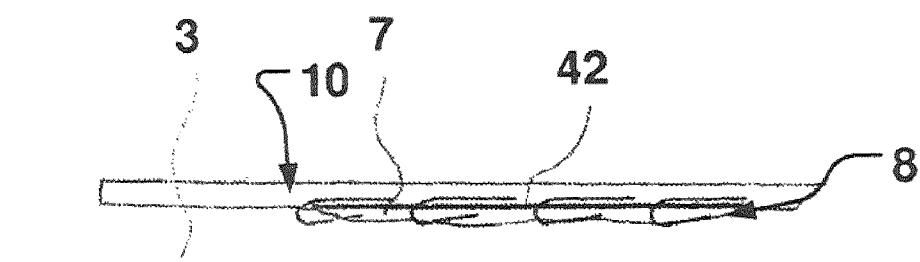

In FIG. 22 the two different results are shown that will result after penetrating a CTO 7 by means of the canalization device when it is covered with a sheet. FIG. 22*a* shows a case where the sheet 42 was attached to the inner surface of the canalization device at the time of implant, and afterwards the outside in turnover, the sheet 42 is now on the outside on the canalization device. When the sheet 42 was attached on the outside at the time of implant, the sheet will appear inside of the stent struts 4 but outside of the extensions in relation to the lumen, as shown in FIG. 22*b*.

Figure 23:
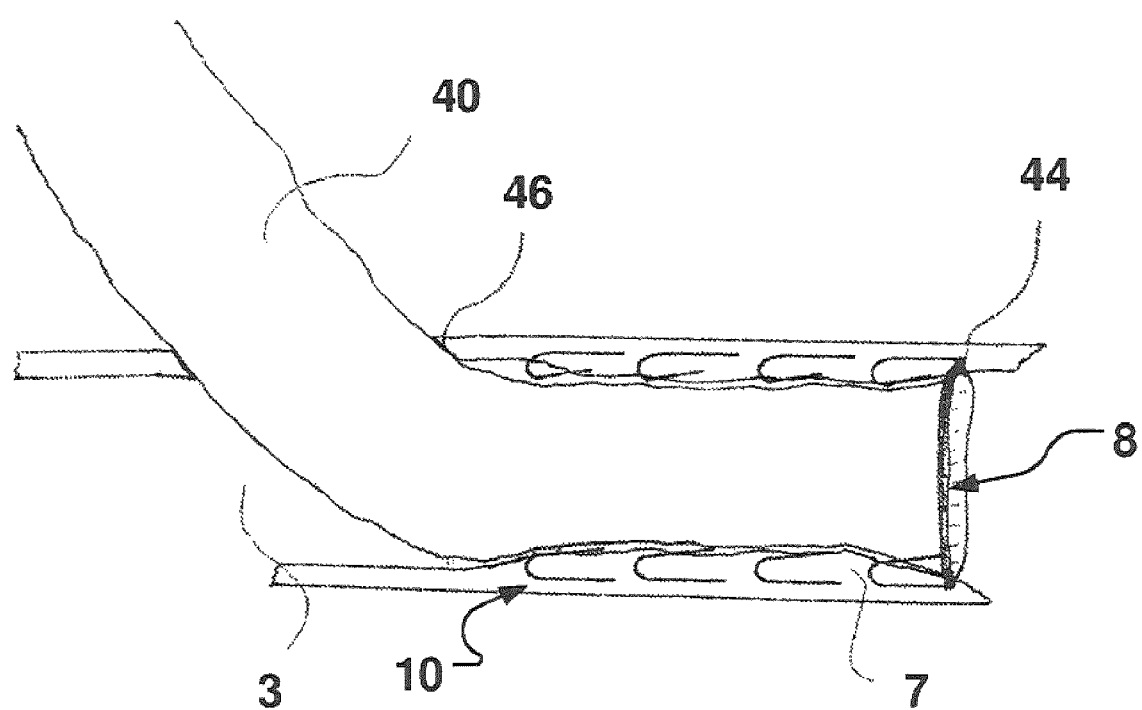

FIG. 23 shows a canalization device after deployment in a coronary artery attached to a vascular graft 40, of native biological or artificial synthetic material. In this case the attachment to the front end 8 of the canalization device at a position 44, which is also shown in FIG. 14 *c*. The FIG. 23 indicates that in the case of attachment to a vascular graft, the insertion into the artery might also be done sideways, directly into the artery 3 rather than all the way through its lumen.

In summary, embodiments of the invention provide for
  a canalization device that does not need an open channel or
    an opening in an occluded lumen before insertion, which
    is not possible with an ordinary stent—hitherto the
    occluded site had to be opened, e.g. by a drill or rather
    rigid guidewire;

extensions of the canalization device that have an advantageous shape, like: spikes, loops, triangles, blades, which furthermore have sharp edges in the front. The extensions are located on the inside of the canalization device when implanted, thus preventing tissue damage upon finalized implantation;

spontaneous inversion of the canalization device outside in is provided due to built in memory characteristics of the device, either by a shape memory or elasticity/resiliency effect;

the canalization device is able to pull itself into solid tissue, which is advantageous as only the initial transition of states is triggered and the remaining tissue penetration may be provided automatically in manner controlled by the design of the device;

the canalization device is able to pull itself out of the delivery catheter;

the canalization device is steerable by means of a bended delivery catheter, whereby narrow passages a reachable for tissue penetration;

the canalization device may have a pre-bent curved shape in some embodiments, thus allowing for controlled, arcuated penetration of tissue;

the canalization device may in some embodiments be positionable in bended lumens for recanalization thereof;

a balloon attached to the front end of the canalization device in some embodiments will be in the front after insertion (and the outside in turning), which is an enormous advantage, since balloon penetration is one of the most difficult actions in CTO penetration;

a guide wire attached to the front end of the canalization device in some embodiments that will be in the front after insertion, and outside in turning, is a huge advantage since guide wire penetration is a must and is also very difficult in the present methods for CTO penetration.

fixation of a graft in the front end of the canalization device in some embodiments that will be in the front after insertion, and turning outside in, may cover the channel from the inside, which allows for attachment of grafts;

a balloon attached in some embodiments is automatically detached by turnaround of the last strut of the canalization device, leaving the balloon tip loose at the front of the created channel;

a guidewire attached in some embodiments is automatically detached by turnaround of last strut of the canalization device leaving the guidewire loose at the front of the created channel;

a vascular graft may in some embodiments be fixed to the front end of the of the canalization device, leaving the graft fixed at the front of the implant inside the created channel;

the canalization device may in some embodiments be provided with a cover with sheets arranged inside thereof;

the canalization device may in some embodiments be provided with a cover with sheets arranged outside thereof; and/or tissue may in some embodiments be foreshortened over a long time by growth in device diameter and thereby a shortening of length of the canalization device after implantation.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention as defined in the appended patent claims.

The invention claimed is:

1. A method of tissue penetration and/or shaping of channels in tissue, or connections between tissue compartments in a body portion by means of a medical device for canalization thereof by penetration thereof, said method comprising:
delivering said medical device in a delivery catheter to said body portion;
pushing a rear end of said medical device initially out of a distal end of said delivery catheter, whereby said medical device turns around a distal end of said delivery catheter, expands, engages with said tissue, and pulls itself by means of its own force out of said delivery catheter, digging and/or cutting into said tissue and turning itself outside in, and advancing into said tissue.

2. The method according to claim 1, further comprising pushing on an outside end of said delivery catheter to ensure that said distal end of said delivery catheter follows the medical device inside said tissue.

3. The method according to claim 1, wherein said tissue at said body portion is solid, or has no channel or opening, or is occluded, before insertion of said medical device.

4. The method according to claim 1, wherein a balloon is simultaneously pulled by the medical device, following the medical device into said body portion.

5. The method according to claim 1, wherein a guidewire is releasably attached to said medical device and simultaneously pulled by the medical device, following the medical device into said body portion.

6. The method according to claim 1, wherein a vascular graft, of native biological or artificial synthetic material, is attached to said medical device and simultaneously pulled by the medical device, following the medical device into said body portion.

7. The method according to claim 6, comprising inserting said medical device sideways into said body portion.

8. The method according to claim 7, comprising creating a bypass of a chronic total occlusion parallel to the native course of the vessel.

9. The method according to claim 6, comprising creating a bypass of a chronic total occlusion parallel to the native course of the vessel.

10. The method according to claim 1, comprising withdrawing said delivery catheter when penetration of the tissue is complete and a channel is created in the tissue, said balloon is centered in said channel, and inflating said balloon for distending said channel, which has hitherto been created by the medical device to a larger lumen, and thereby distending said medical device.

11. The method according to claim 1, comprising inflating a balloon of said delivery catheter when penetration of the tissue is complete and a channel is created in the tissue, thus distending said channel, which has hitherto been created by the medical device to a larger lumen, and thereby distending said medical device.

12. The method according to claim 1, comprising prohibiting creation of debris and loose parts, or fixating such debris and loose parts, by said device.

13. The method according to claim 1, wherein said body portion comprises an artery.

14. The method according to claim 13, wherein said body portion comprises a chronic total occlusion of a coronary artery, said method comprising holding plaque material of said chronic total occlusion compressed and together by the medical device after penetration thereof through said chronic total occlusion, after recanalization of the chronic total occlusion.

15. The method according to claim 1, comprising covering walls of a channel created with a sheet attached inside or outside to said medical device and thereby sealing off radial leakage through said medical device and prohibiting creation of debris and loose parts, or fixating such debris and loose parts.

16. The method according to claim 15, comprising inserting said medical device sideways into said body portion.

17. The method according to claim 15, comprising creating a bypass of a chronic total occlusion parallel to the native course of the vessel.

18. The method according to claim 1, comprising digging and/or cutting with extensions of said medical device through a fibrous cap of a chronic total occlusion during said penetration.

19. The method according to claim 1, comprising steerably bending a steerably bendable catheter portion of said delivery catheter for curved canalization of said body portion.

20. The method according to claim 1, wherein said body portion is liver tissue and said method comprises canalization of said liver tissue.

21. The method according to claim 20, wherein said canalization is made between the porta vein and the inferior vena cava in order to allow blood to flow from the porta system to the cava system in order to treat portal hypertension.

22. The method according to claim 21, wherein said canalization is made through obstructions to treat biliary stasis.

23. The method according to claim 20, comprising covering walls of a channel created with a sheet attached inside or outside to said medical device and thereby sealing off radial leakage through said medical device and prohibiting creation of debris and/or loose parts, or fixating such debris and/or loose parts.

24. The method according to claim 1, wherein said body portion comprises cancer tissue, and said method comprises creating connections in said tissue for palliation.

25. The method according to claim 24, wherein said body portion is in the esophagus.

* * * * *